United States Patent

Christensen et al.

[11] 4,234,596
[45] Nov. 18, 1980

[54] 3-(2-AMINOETHYLTHIO)-6-(1-HYDROXYETHYL)-7-OXO-1-AZABICYCLO[3.2.0]HEPT-2-ENE-2-CARBOXYLIC ACID

[75] Inventors: Burton G. Christensen, Scotch Plains; David B. R. Johnston, Warren; Susan M. Schmitt, Scotch Plains, all of N.J.

[73] Assignee: Merck & Co., Inc., Rahway, N.J.

[21] Appl. No.: 17,680

[22] Filed: Mar. 5, 1979

Related U.S. Application Data

[63] Continuation-in-part of Ser. No. 833,210, Sep. 15, 1977, abandoned, which is a continuation-in-part of Ser. No. 743,365, Nov. 19, 1976, abandoned, and Ser. No. 792,071, Apr. 28, 1977, abandoned.

[51] Int. Cl.² .................... C07D 487/04; A61K 31/40
[52] U.S. Cl. .................. 424/274; 260/239 A; 260/245.2 T; 542/416; 544/90; 424/114
[58] Field of Search ....... 260/326.31, 239 A, 245.2 T; 424/274; 542/416

[56] References Cited

U.S. PATENT DOCUMENTS 3,950,357  4/1976  Kahan et al. .................... 260/326.31

Primary Examiner—Mary C. Lee
Attorney, Agent, or Firm—James A. Arno; Julian S. Levitt

[57] ABSTRACT

Isomeric forms of 3-(2-aminoethylthio)-6-(1-hydroxyethyl)-7-oxo-1-azabicyclo[3.2.0]hept-2-ene-2-carboxylic acid (I)

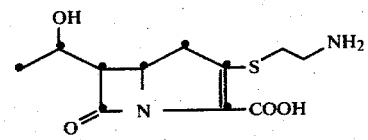

are disclosed; also disclosed is a process for their total synthesis; such isomers individually, and as mixtures, are useful as antibiotics.

12 Claims, No Drawings

3-(2-AMINOETHYLTHIO)-6-(1-HYDROXYE-THYL)-7-OXO-1-AZABICYCLO[3.2.0]HEPT-2-ENE-2-CARBOXYLIC ACID

BACKGROUND OF THE INVENTION

This is a continuation-in-part of U.S. Ser. No. 833,210 filed 9-15-77 which in turn is a continuation-in-part of U.S. Ser. Nos. 743,365 (filed 11-19-76) and 792,071 (filed 4-28-77) all now abandoned.

This invention relates to the total synthesis of the antibiotic 3-(2-aminoethylthio)-6-(1-hydroxyethyl)-7-oxo-1-azabicyclo[3.2.0]hept-2-ene-2-carboxylic acid (I), otherwise known as thienamycin, which is disclosed and claimed in U.S. Pat. No. 3,950,357 issued Apr. 13, 1976. This patent is incorporated herein by reference as it relates to the utility of I as an antibiotic in animal and human therapy and in inanimate systems. This invention also relates to all novel isomeric forms of I, which isomeric forms, individually and as mixtures, are useful as antibiotics.

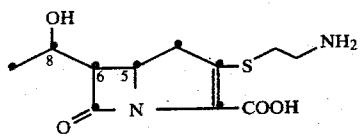

It should be noted that the absolute configuration of thienamycin is 5R,6S,8R. Two other thienamycin isomers are known. They are useful as antibiotics and are isolated as natural products of fermentation. These isomers, known as "desacetyl 890A$_1$" and "desacetyl 890A$_3$" are disclosed and claimed in co-pending, commonly assigned, U.S. patent application Ser. No. 734,584 filed Oct. 21, 1976, now abandoned. [The corresponding N-acetyl fermentation product derivatives are known as 890A$_1$ and 890A$_3$, respectively, and are disclosed and claimed in co-pending, commonly assigned U.S. patent application Ser. No. 634,300 filed Nov. 21, 1975, now abandoned.] Desacetyl 890A$_3$ has been assigned the absolute configuration 5R,6S,8S; desacetyl 890A$_1$ has been assigned the absolute configuration 5R,6R,8S. Thus from fermentation, three of the possible eight thienamycin isomers are known. The remaining five isomers may be designated, relative to structure I, by absolute configuration: 5R,6R,8R; 5S,6S,8S; 5S,6S,8R; 5,6R,8S; and 5S,6R,8R. However, by practice of the total synthesis disclosed and claimed herein all isomers of I are made available as a mixture of the 4 diastereoisomers which mixture possesses antibacterial activity and which mixture is amenable to resolution by conventional techniques to provide any desired isomer in substantially pure form. Thus, for example, when resolving the mixture, the 4 diastereoisomers (2 cis, 2 trans) are separable by chromatography; and resolution of any given d/l pair with optically active acids or bases proceeds according to conventional techniques. Alternatively, the total synthesis disclosed herein may be conducted in a stereo-selective manner to provide any given isomer.

This invention also relates to the pharmaceutically acceptable salt derivatives of I; pharmaceutical compositions comprising I and such derivatives; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which are isomers of the antibiotic thienamycin. These antibiotics are active against a broad range of pathogens which representatively include both gram positive bacteria such as *S. aureus, Strep. pyogenes* and *B. subtilis* and gram negative bacteria such as *E. coli, Proteus morganii*, Serratia, Pseudomonas and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) may unambiguously be identified by absolute configuration when referenced against the numbering system of structure I. The following projection drawings may be helpful in visualizing the compounds (isomers) in question:

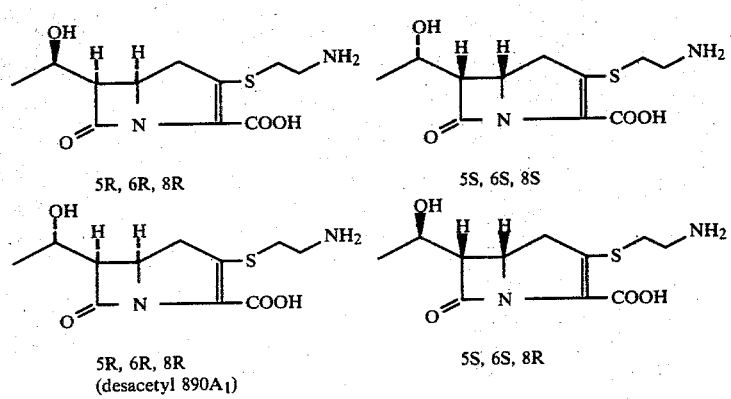

5R, 6R, 8R    5S, 6S, 8S 5R, 6R, 8R
(desacetyl 890A$_1$)    5S, 6S, 8R

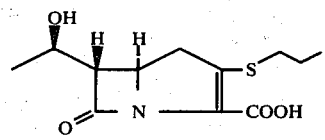
natural fermentation product, "thienamycin"
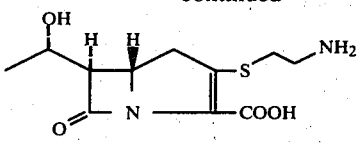
5S, 6R, 8S
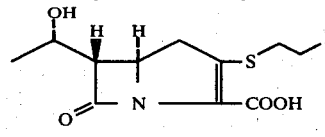
5R, 6S, 8S
(desacetyl 890A$_3$)
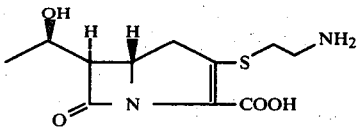
5S, 6R, 8R
The total synthesis of the present invention which provides the above illustrated species may conveniently be summarized by the following reaction diagram:
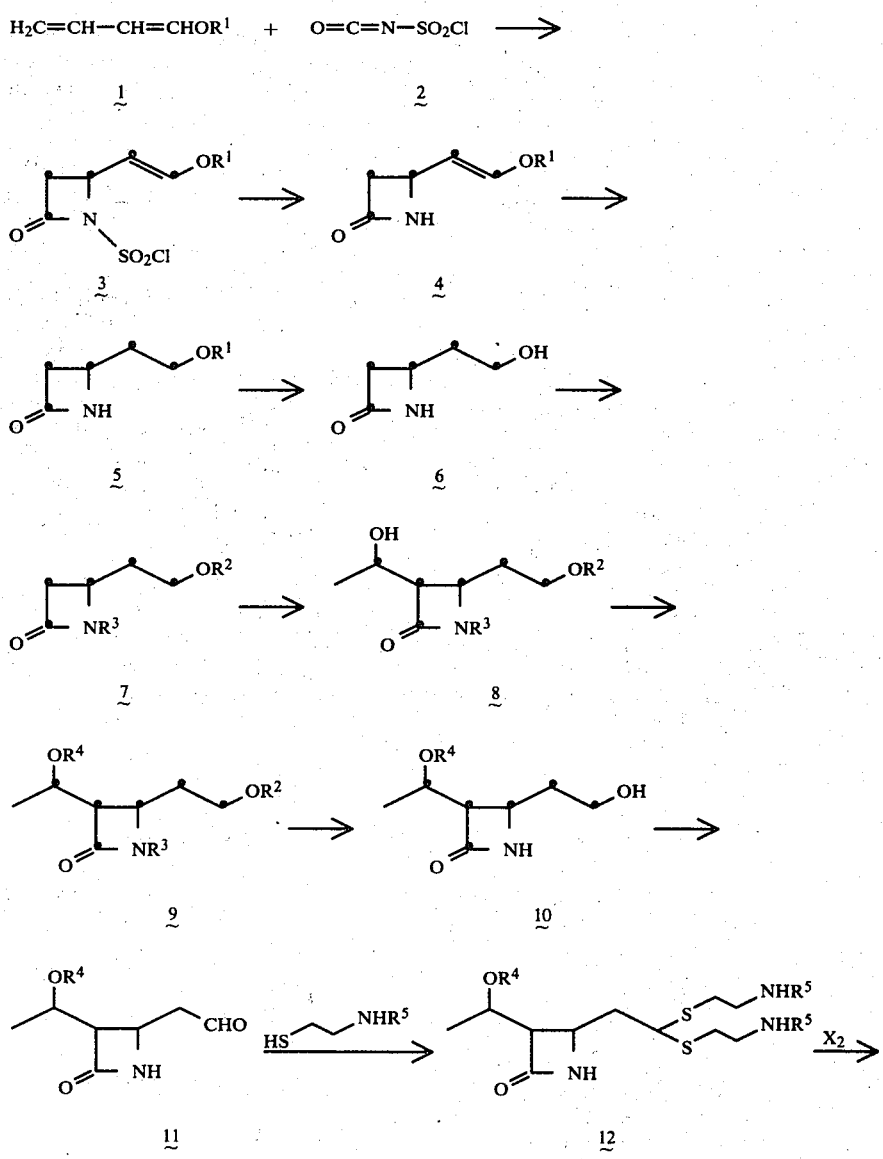

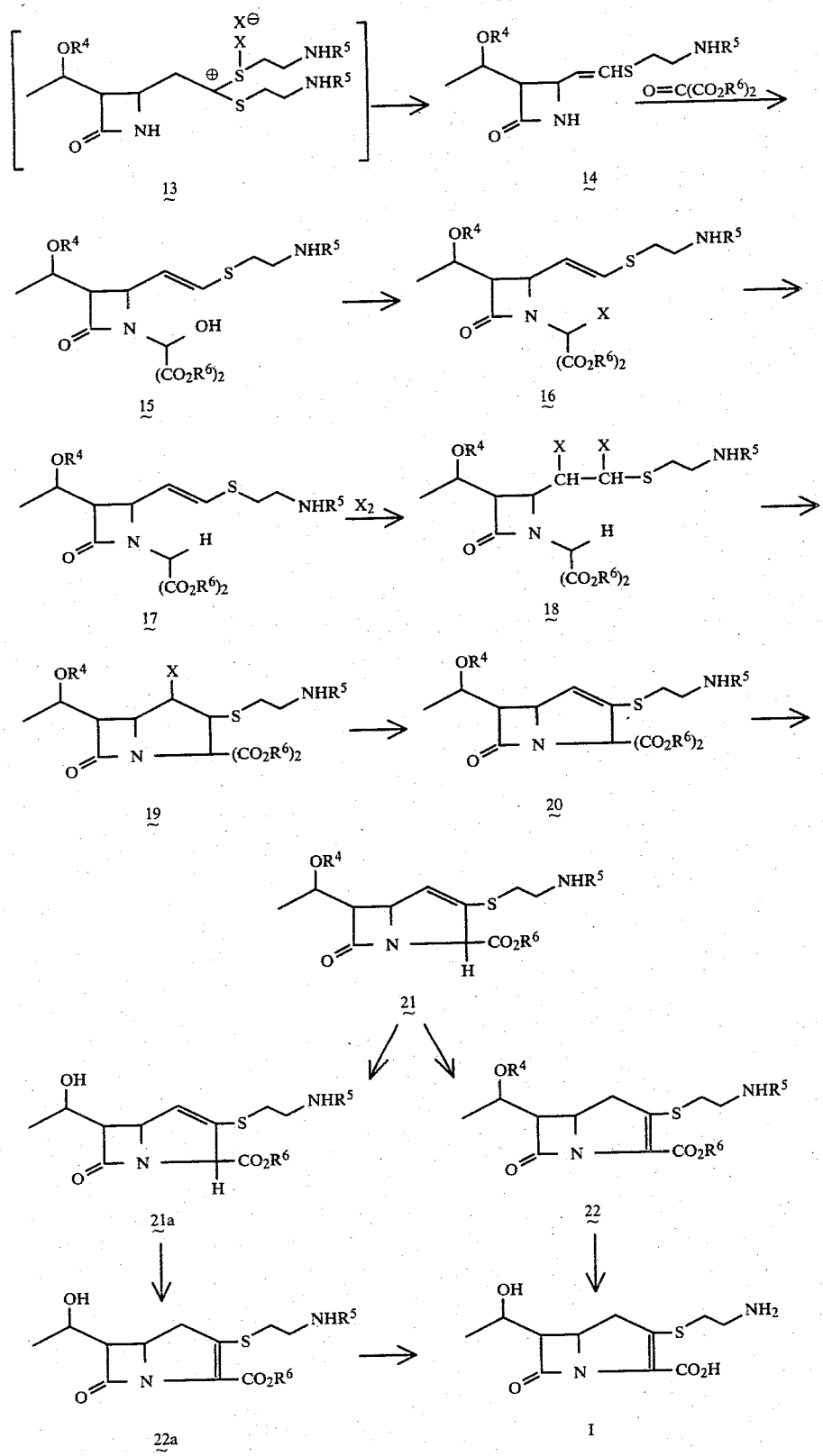
In words relative to the above diagram, the 4-(2-substituted-vinyl)azetidine-2-one, 4, starting material is prepared by reacting an $R^1$-oxybutadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical $R^1$ is an easily removable acyl blocking group such as an alkanoyl or aralkanoyl which bears no functional group or groups which might interfere with the desired course of reaction ($\underline{1}+\underline{2}\rightarrow\underline{3}\rightarrow\underline{4}$). Intermediate species 3 is converted to the sulfinamide by reduction which is then hydrolyzed to 4 at pH 6-8. Typically the reaction solution comprising 3 is contacted (5-30 minutes) with an aqueous solution (at 0°-25° C.) of a reducing agent such as sodium sulfite, thiophenol, or the like, at pH 6-8 to provide 4.

The reaction $\underline{4}\rightarrow\underline{5}$ is a reduction, and is preferably achieved by hydrogenation in a solvent such as ethyl acetate ether, dioxane, tetrahydrofuran (THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The de-blocking reaction $\underline{5}\rightarrow\underline{6}$ is usually desirable when $R^1$ is acyl to permit the later alkylation, $\underline{7}\rightarrow\underline{8}$. The preferred de-blocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from $-10°$ to 25° C.

Blocking groups $R^3$ and $R^2$ are established ($\underline{6}\rightarrow\underline{7}$) to provide a suitably protected species for alkylation ($\underline{7}\rightarrow\underline{8}$). There is no criticality in the choice of blocking groups, provided only that they do not interfere with the intended alkylation. $R^3$ may be hydrogen, a triorganosilyl group such as trimethylsilyl or the like, or a cyclic ether such as 2-tetrahydropyranyl; $R^2$ may also be a cyclic ether such as 2-tetrahydropyranyl; alternatively $R^3$ and $R^2$ may be joined together to form protected species such as 7a:

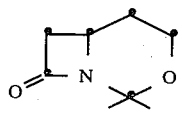

For example, species such as 7a are conveniently prepared by treating 6 with 2,2-dimethoxypropane in the presence of a catalyst such as boron trifluoride etherate, toluene sulphonic acid, or the like in a solvent such as methylene chloride, ether, chloroform, dioxane or the like at a temperature of from $-10°$ C. to 35° C. for from a few minutes to 1 hour.

The alkylation ($\underline{7}\rightarrow\underline{8}$) is preferably conducted by treating 7 with a strong base such as lithium diisopropylamide, sodium amide, potassium hydride or the like in a solvent such as THF, glyme, ether, dimethylformamide(DMF), dimethylsulfoxide(DMSO) or the like at a temperature of from $-78°$ C. to 0° C. The resulting anion is then treated with excess acetaldehyde to provide 8.

The reaction $\underline{8}\rightarrow\underline{9}$ establishes the blocking group $R^4$ and is typically accomplished by treating 8 with a base such as an alkali metal hydroxide, lithium diisopropyl amide 4-dimethylaminopyridine, or n-butyllithium in a solvent such as ether, THF, dioxane, DMF, DMSO or the like, followed by treatment with an acyl halide of choice such as an alkanoyl, aralkanoyl or nuclear substituted aralkanoyl, or alkyl, aryl or aralkyl, substituted aralkyl or substituted aryl haloformate such as p-nitrobenzylchloroformate or the like at a temperature of from $-78°$ C. to 25° C. for from 1-24 hours.

The de-blocking reaction $\underline{9}\rightarrow\underline{10}$ is typically conducted by acid hydrolysis such as aqueous acetic acid at a temperature of from 25° C. to 75° C. for from 5 minutes to 3 hours.

The aldehyde intermediate 11 is prepared by treating 10 with an oxidizing agent such as $CrO_3.2$(pyridine) in $CH_3CN$, 1:1 mixture of dimethylsulfoxide and acetic anhydride, cyclohexylcarbodiimide in DMSO or the like at a temperature of from 0°-25° C. for from 5 minutes to 1 hour. The resulting species 11 in a solvent such acetonitrile, methylene chloride, chloroform or the like at a temperature of from $-10°$ to 25° C. is treated with an excess of N-blocked cysteamine, $HSCH_2$—$CH_2NHR^5$, in the presence of an acid catalyst such as boron trifluoride etherate, toluene sulphonic acid or the like to provide 12. Typically, the reaction requires from 1 to 60 minutes. There is no criticality as to the identity of the N-protecting group, $R^5$, on the cysteamine reagent and suitable groups are p-nitrobenzyloxycarbonyl, o-nitrobenzyloxycarbonyl, t-butyloxycarbonyl, 2,2,2-trichloroethoxycarbonyl, phthaloyl, or the like.

The vinyl sulphide 14 is obtained via intermediate 13 by treating 12 with a halogen such as chlorine or bromine (X=Cl or Br) in a solvent such as ether, methylene chloride, tetrahydrofuran, glyme or the like at a temperature of from $-78°$ to 30° C. for from 1 to 30 minutes, followed immediately by treating with an olefin such as cyclohexene, isobutylene, or the like followed by treatment with a base such as triethylamine, DBU, sodium hydride, or the like in a solvent such as DMF, glyme, THF, HMPA. The solution is held at $-20°$ to 25° C. for from 1 to 8 hours to yield 14.

The vinyl sulphide species 14 is reacted with a diester of oxomalonic acid (or its monohydrate) to provide 15. There is no criticality as to the identity of the ester moiety, $R^6$, of the oxomalonic acid. $R^6$ may be a conventional, easily removable blocking group or it may be a pharmaceutically acceptable ester moiety. Suitable ester radicals $R^6$ are p-nitrobenzyl, benzyl, o-nitrobenzyl, t-butyl, 2,2,2-trichloroethyl. The reaction $\underline{14}\rightarrow\underline{15}$ is typically conducted in a high boiling organic solvent such as benzene, toluene, cyclohexane, halo aromatic or the like at a temperature of from about 50° C. to reflux for from 0.5 to 6 hours.

The halogenation reaction $\underline{15}\rightarrow\underline{16}$ is typically conducted in a solvent such as THF, glyme, ether, methylene chloride, chloroform or the like in the presence of a halogenating agent such as thionyl chloride, phosphorous pentachloride or the like in the presence of base such as pyridine at a temperature of from $-20°$ to 25° C. for from 5 minutes to 3 hours. The selective reduction of $\underline{15}\rightarrow\underline{17}$ via 16 is completed by treating 16 with tributylphosphine, triphenylphosphine or the like in aqueous DMF or similar aqueous systems involving dioxane, THF, glyme, DMSO, or acetone in the presence of $K_2HPO_4$ at a temperature of from about 0°-50° C. for from 10 minutes to 5 hours.

Species 17 is halogenated by the previous procedure ($\underline{12}\rightarrow\underline{13}$), but omitting the addition of the cyclohexene or other olefin, to provide the dihalo species 18. Species 18 is treated with a base such as triethylamine, sodium hydride or potassium hydride in a solvent such as DMF, acetonitrile, methylene chloride, chloroform, glyme or the like at a temperature of from about $-78°$ to 25° C. for 1 to 5 hours to provide 19. Species 19 is converted to 20 on treatment with a strong base such as 1,5-diazabicyclo[5.4.0]-undec-5-ene(DBU), 1,5-diazabicyclo[3.4.0]non-5-ene(DBN), or the like in a solvent such as DMSO, acetone, chloroform, DMF THF, glyme or the like or on treatment with AgF in pyridine at a temperature of from 0°–40° C. for from ¼ to 24 hours. The reaction 20→21 is conducted by treating 20 with an aromatic base such as pyridine, s-collidine or lutidine, in the presence of a displacing agent such as lithium iodide, lithium bromide, sodium bromide, or the like at a temperature of from about 80°–150° C. for from 15 minutes to 2 hours. An aqueous work up of the resulting reaction mixture provides 21. Isomerization of the double bond 21→22 is accomplished by treating 21 in a solvent such as DMF, DMSO, ethyl ether, THF, glyme, methylene chloride with a base such as diisopropylamine, DBU, DBN, or the like at a temperature of from 0° to about 25° C. for from a few minutes to 2 hours or until equilibium has been established as determined by examination of sample aliquots by ultraviolet absorption or by thin layer chromatography. The final reaction 22→I (by hydrogenolysis of the blocking groups) is accomplished by treating 22 in a solvent such as dioxane, ethanol, THF or the like or an aqueous mixture thereof in the presence of a Platinum metal catalyst such as Pd/C under a hydrogen pressure of from 1–4 atmospheres for from 0.5 to 8 hours at a temperature of from about 0°–25° C.

Alternatively the blocking group, R₄, may be selected such that 21 can be selectively deblocked to 21a. For example, R₄ may be chosen to be o-nitrobenzyloxycarbonyl so that a solution of 21 in CHCl₃, dioxane or the like may be photolyzed at 3000–4000 A for a period of 0.5 to 5 hours to give 21a. Isomerization of the double bond 21a→22a is carried out as above for 21→22. The final conversion 22a→I (by hydrogenolysis of the remaining blocking groups) is carried out as for 22→I.

The above-described total synthesis may also advantageously start with 4-vinyl azetidinone[(23), below; E. J. Moriconi, W. C. Meyer, J. Org. Chem., 36, 2841 (1971)] rather than the enol acylate azetidinone (4, above). This variation in the total synthesis has the advantage of conveniently imparting stereo-selectivity to the process at an early stage. The stereo-chemistry of the present invention is discussed fully below. The following scheme illustrates this 4-vinyl azetidinone embodiment of the present invention; notice that it ties into the above scheme at species 14.

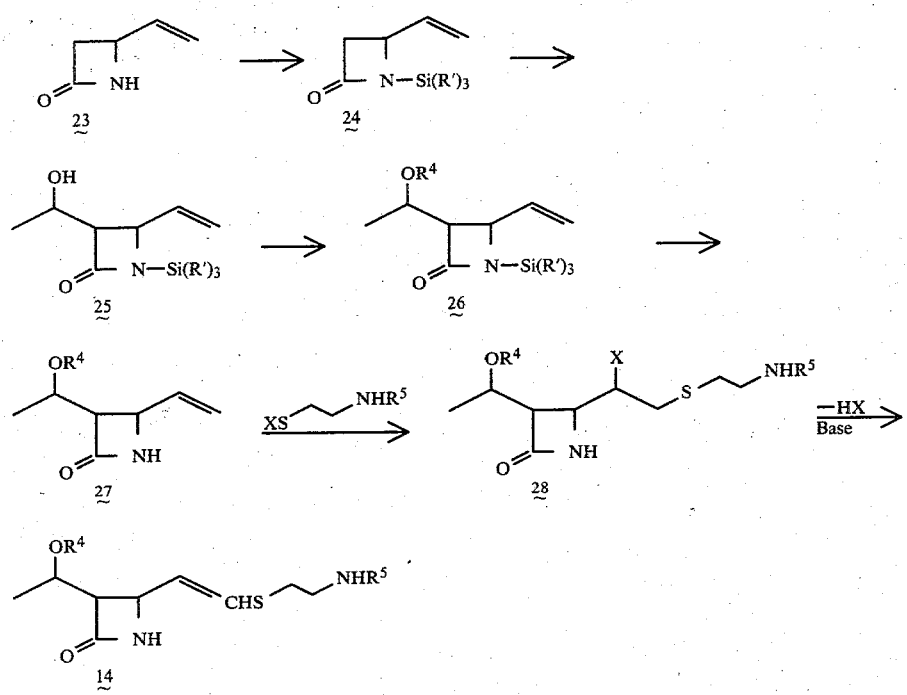

In words relative to the above reaction diagram, 4-vinyl azetidinone 23 is silylated to provide the N-silyl species 24. The groups R' on the silyl radical are lower-alkyl having from 1–6 carbon atoms especially preferred triorganosilyl groups are trimethyl silyl and t-butyl-dimethylsilyl. Typically, the silylation (23→24) is achieved by treating 23 in a solvent such as DMF, DMSO, HMPA or the like with the silylating agent of choice, dimethyl t-butylsilyl chloride, and a base such as Et₃N, pyridine, N,N-dimethylaniline and the like at a temperature of from −10° to 30° C. for from 1 to 8 hours. Species 24 is alkylated to form 25 by treatment with acetaldehyde in the presence of base. This reaction 24→25 is conducted exactly as described above for the alkylation 7→8. The O-protecting group is established in the reaction 25→26. The protecting group R⁴ is as previously defined and the reaction 25→26 is exactly analogous to the above described reaction 8→9. It should be noted here, and will be developed below that the reactions (24→25) and (25→26) represent convenient opportunities to separate species 25 and 26 into the four racemic diastereoisomers. The removal of the N-triorganosilyl group is accomplished in reaction 26→27 by mild acid catalyzed solvolysis. The halo sulfide species 28 is obtained from 27 by treating 27 in a solvent such as methylene chloride, THF, glyme, or the like with the reagent XSCH₂CH₂NHR⁵ wherein R⁵ has previously been defined and X is halogen such as chloro or bromo at a temperature of from −50° to 50° C. for from 1 to 16 hours. The final sulfide intermediate 14, which is common to the above illustrated scheme of total synthesis is obtained from 28 by elimination of HX on treatment of 28 with a base such as 1,5-diazabicyclo[5.4.0]undec-5-ene (DBU), 1,5-diazabicyclo[4.3.0]-non-5-ene, (DBN), 1,4-diazabicyclo[2.2.2]octane, (DABCO), or silver fluoride in a solvent such as DMSO, pyridine DMF, HMPA or the like at a temperature of from −20° to 50° C. for from ¼ to 16 hours.

Another procedure for the total synthesis employs an azide radical rather than the protected amino, which route is illustrated above. The following diagram illustrate the azide route; wherein the starting material is the previously defined species 11:

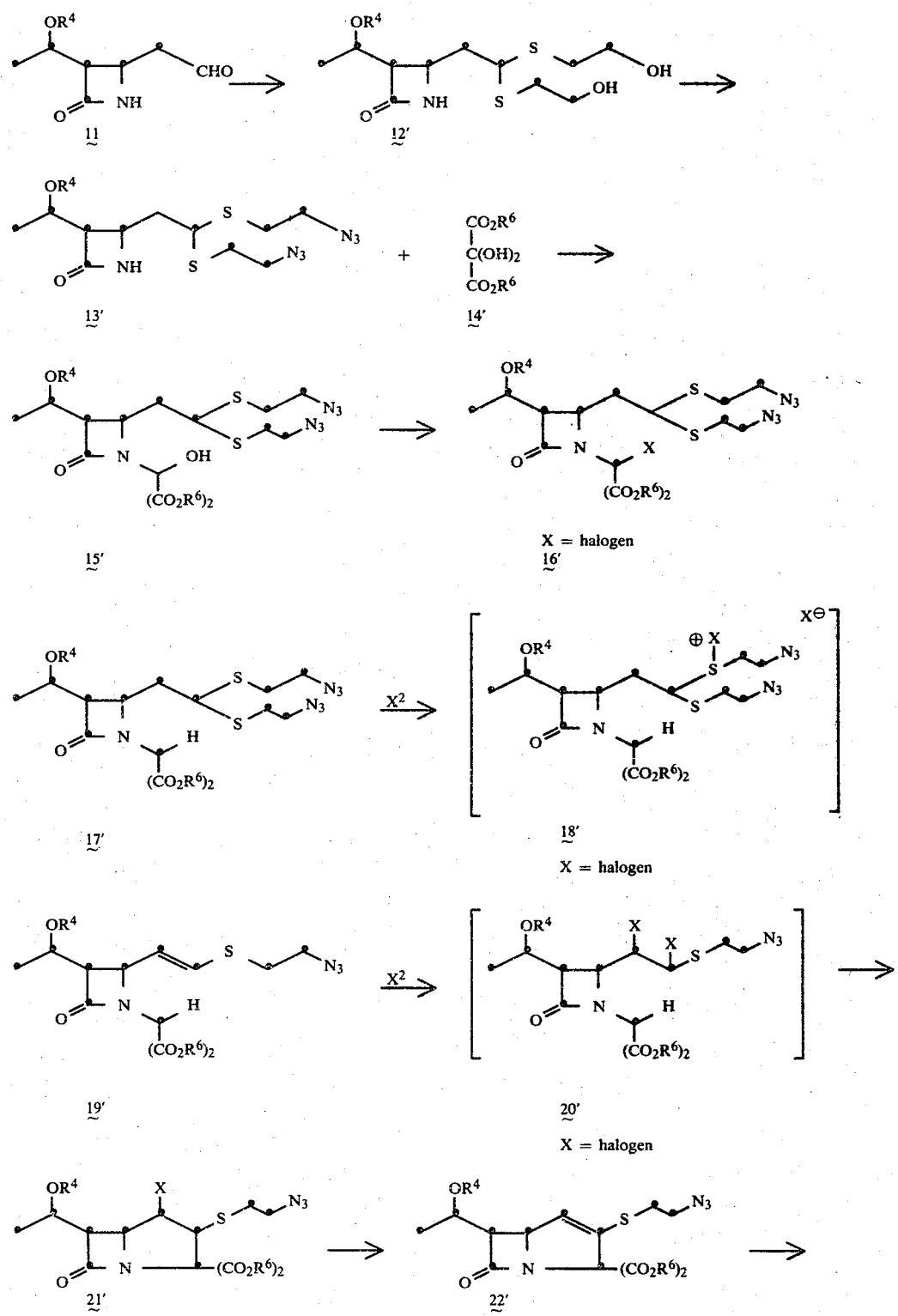

-continued

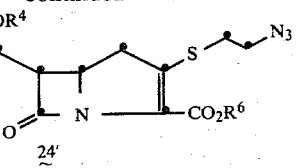
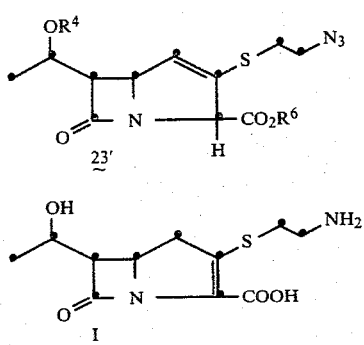

In words relative to the above diagram, the aldehyde intermediate 11 in a solvent such as acetonitrile, ehtylenechloride, chloroform or the like at a temperature of from −10° to 25° C. is treated with an excess of 2-mercaptoethanol in the presence of an acid catalyst such as boron trifluoride etherate, toluene sulphonic acid or the like to provide 12'. Typically, the reaction requires from 1 to 30 minutes.

The diazide species 13' is formed from 12' by treating 12' in a solvent such as THF, chloroform, methylene chloride, ether or the like with an esterifying agent such as mesyl chloride, tosyl chloride, benzenesulfonylchloride, triflyl chloride, or the like in the presence of base such as triethylamine, pyridine, dimethylalanine, potassium carbonate or the like. The resulting diester, which optionally may be isolated, is treated in a solvent such as DMSO, DMF or the like with an excess of sodium azide at a temperature of from about 0°–35° C. for a period from about 1–24 hours to provide 13'.

The diazide species 13' is reacted with a diester of the monohydrate of oxomalonic acid to provide 15'. There is no criticality as to the identity of the ester moiety, $R^6$, of the oxomalonic acid. $R^6$ may be a conventional, easily removable blocking group or it may be a pharmaceutically acceptable ester moiety. A suitable ester radical $R^6$ is p-nitrobenzyl. The reaction 13'+14'→15' is typically conducted in a high boiling organic solvent such as toluene cyclohexane, halo aromatic or the like at a temperature of from about 50° C. to reflux for from 0.5 to 6 hours.

The halogenation reaction 15'→16' is typically conducted in a solvent such as THF, glyme, ether, methylenechloride, chloroform or the like in the presence of a halogenated agent such as thionyl chloride, phosphorous pentachloride or the like in the presence of base such as pyridine at a temperature of from −20° to 25° C. for from 5 minutes to 3 hours. The selective reduction of 15'→17' via 16' is completed by treating 16' with triphenylphosphine in aqueous DMF or similar aqueous systems involving dioxane, THF, glyme, DMSO, or acetone in the presence of $K_2HPO_4$ at a temperature of from about 0°–50° C. for from 10 min. to 5 hours.

The halogenation reaction 17'→18' is conducted by treating 17' with bromine or chlorine at a temperature of from about −20° to 0° C. in a solvent such as diethylether/pentane, THF, glyme, methylenechloride, chloroform or the like. Intermediate 18' in a solvent such as DMF, acetonitrile, methylenechloride, chloroform, glyme, THF, or the like in the presence of an acceptor such as cyclohexene and a base such as sodium hydride potassium hydride or trialkylamine at a temperature of from about −20° to 25° C. for from 0.5 to 6 hours yields species 19' which is halogenated by the previous procedure to provide the dihalo species 20'. Species 20' is treated with a base such as sodium hydride or potassium hydride or trialkylamine in a solvent such as DMF, acetonitrile, methylene chloride, chloroform, glyme or the like at a temperature of from about −78° to 25° C. to provide 21'. Species 21' is converted to 22' on treatment with a strong base such as 1,5-diazabicyclo[5.4.0]undec-5-ene(DBU)1,5-diazabicyclo[3.4.0]non-5-ene (DBN), or the like in a solvent such as DMSO, acetone, chloroform, DMF, THF, glyme or the like or on treatment with AgF in pyridine at a temperature of from 0°–40° C. for from 1 to 24 hours. The reaction 22'→23' is conducted by treating 22' with an aromatic base such as pyridine, s-collidine, lutidine or DMF in the presence of a displacing agent such as lithium iodide, lithium bromide, sodium bromide, or the like at a temperature of from about 80°–150° C. for from 15 minutes to 2 hours. An aqueous work up of the resulting reaction solution provides 23'. Isomerization of the double bond 23'→24' is accomplished by treating 23' in a solvent such as DMF, DMSO, ethyl ether, THF, glyme, methylene chloride, with a base such as diisopropylamine, DBU, DBN, or the like at a temperature of from 0° to about 25° C. for from a few minutes to 1 hour or until equilibrium has been established as determined by examination of sample aliquots by ultraviolet absorption or by thin layer chromatography. The final reaction 24'→I (by hydrogenolysis of the blocking group and reduction of the azide) is accomplished by treating 24' in a solvent such as dioxane, ethanol, THF or the like or an aqueous mixture thereof in the presence of a platinum metal catalyst such as $PtO_2$ under a hydrogen pressure of from 1–50 atmospheres for from 0.5 to 8 hours at a temperature of from about 0°–25° C.

Separation of Isomers

Because of the three centers of asymmetry, the thienamycin molecule I, is capable of existing in eight isomeric forms. The four diastereomeric pairs are illustrated above and designated by absolute configuration.

The above-described total synthesis may be conducted in such a manner that all isomers are ultimately obtained as a mixture, or it may be conducted in a stereo-selective way. Such stereo-selective approaches are discussed below. In any event, a given isomeric mixture of I may be resolved into its constituent isomers by application of any of a variety of well-known techniques. For example, the four diastereomers may be separated by chromatography and any given racemic pair of optical isomers may be separated by any of a variety of physico-chemical techniques after forming diastereomeric salts with an optically active acid or base.

In the following schemes of resolution, which impart stereo-selectivity to the above-defined total synthesis, the intermediate species will be numbered as shown in the above reaction diagrams. The stereo configuration of any given species will be designated relative to structure I and its numbering system.

Scheme 1

Central to this scheme is the preparation of 4 from an acyloxy butadiene (1) possessing an optically active acyl moiety, 1+2→[3]→4 wherein R¹ is menthyloxyacetic, or camphoric monomethyl ester, for example. This early resolution and ensuring steps are summarized by the following diagram:

ble bond of the optically active enol acylate may be followed by resolution:

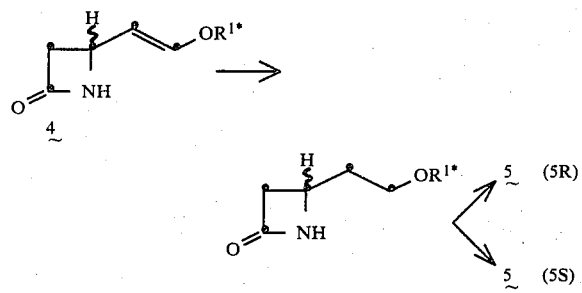

Alternatively, a non optically active enol acylate 4 (e.g.,

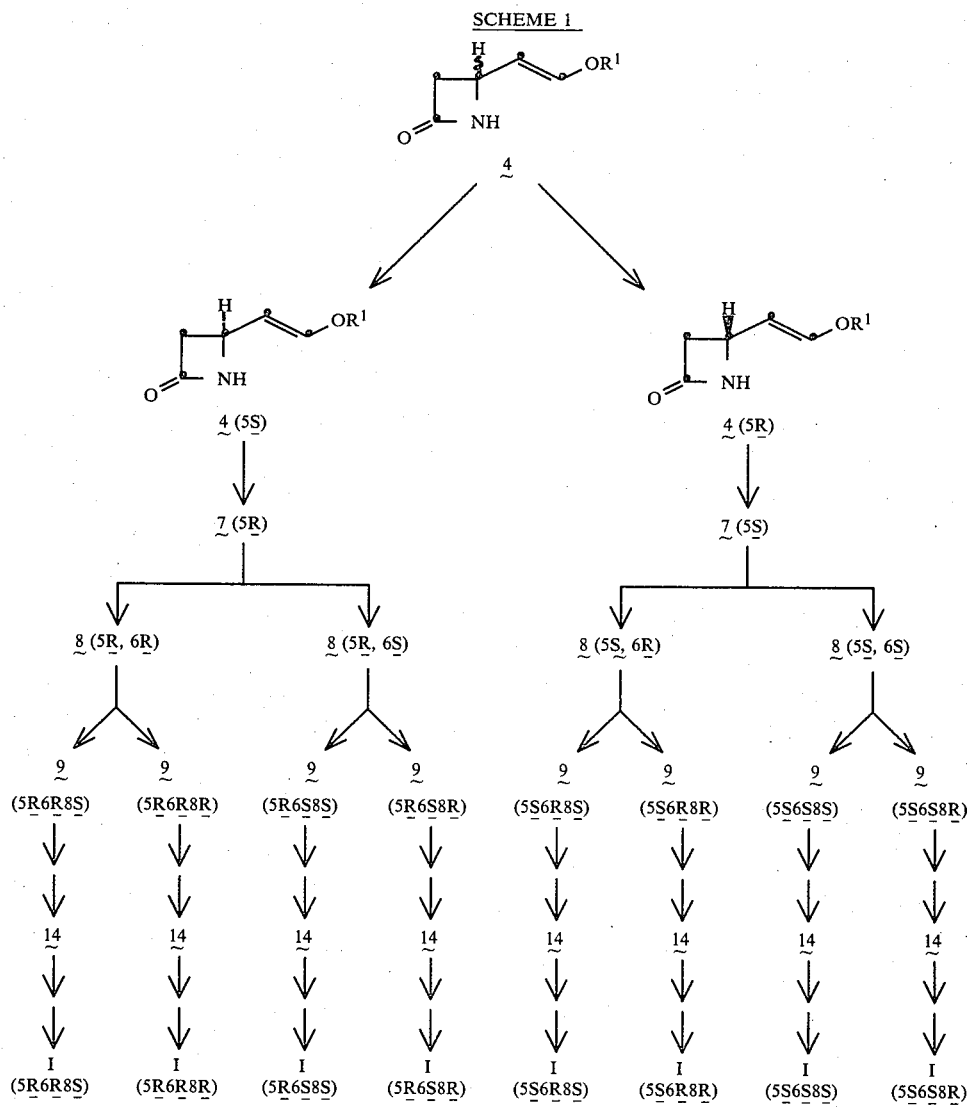

Scheme 2

Central to this scheme is the acylation of the 2'-hydroxyethyl side chain of 4 with an optically active acid such as menthoxyacetic, camphoric or the like. Resolution of the resulting species may be carried out at several stages. For example, hydrogenation of the dou- enol acetate) can be hydrogenated, saponified and re-esterified with an optically active acid and then resolved as shown above. Another alternative is to delay resolution until formation of species 10

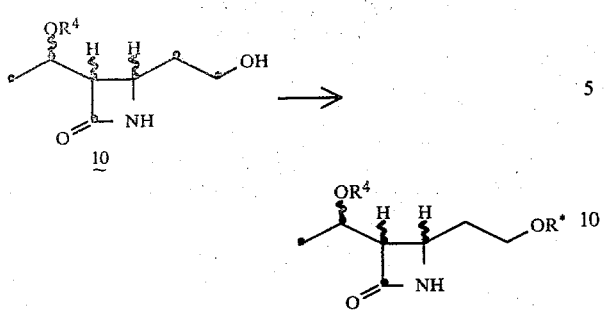

wherein R* is optically active. Resolution of this intermediate provides: 10(5R,6R,8S); 10(5S,6S,8R); 10(5R,6R,8R); 10(5S,6S,8S); 10(5R,6S,8S); 10(5S,6R,8R); 10(5R,6S,8R); and 10(5S,6R,8S). Once any of the above resolutions has been achieved, the acyl group is saponified off and the synthesis proceeds.

Scheme 3

The vinyl azetidinone starting material species 23 is a known compound and is resolvable into its optical isomers by known procedures. See for example, British Patent 1,273,278 which is incorporated herein by reference. The following diagram outlines a stereo-selective synthesis employing as starting material a pure optical isomer of vinyl azetidinone.

lowed by alkylation provides 25(5R,6R), 25(5R,6S), 25(5S,6R), and 25(5S,6S) via species 24. Species 25 are separable by physical or chemical methods such as chromatography. Following establishment of the protecting group R⁴, species 26 are separable into: 26(5R,6R,8R); 26(5R,6R,8S); 26(5R,6S,8R); 26(5R,6S,8S); 26(5S,6R,8R); 26(5S,6R,8S); 26(5S,6S,8R); and 26(5S,6S,8S) by chromatography. The synthesis may now proceed as illustrated above to provide I(5R,6R,8R); I(5R,6R,8S); I(5R,6S,8R); I(5R,6S,8S); I(5S,6R,8R); I(5S,6R,8S); I(5S,6S,8R); and I(5S,6S,8S), each in substantially pure form.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary ot tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, etha-

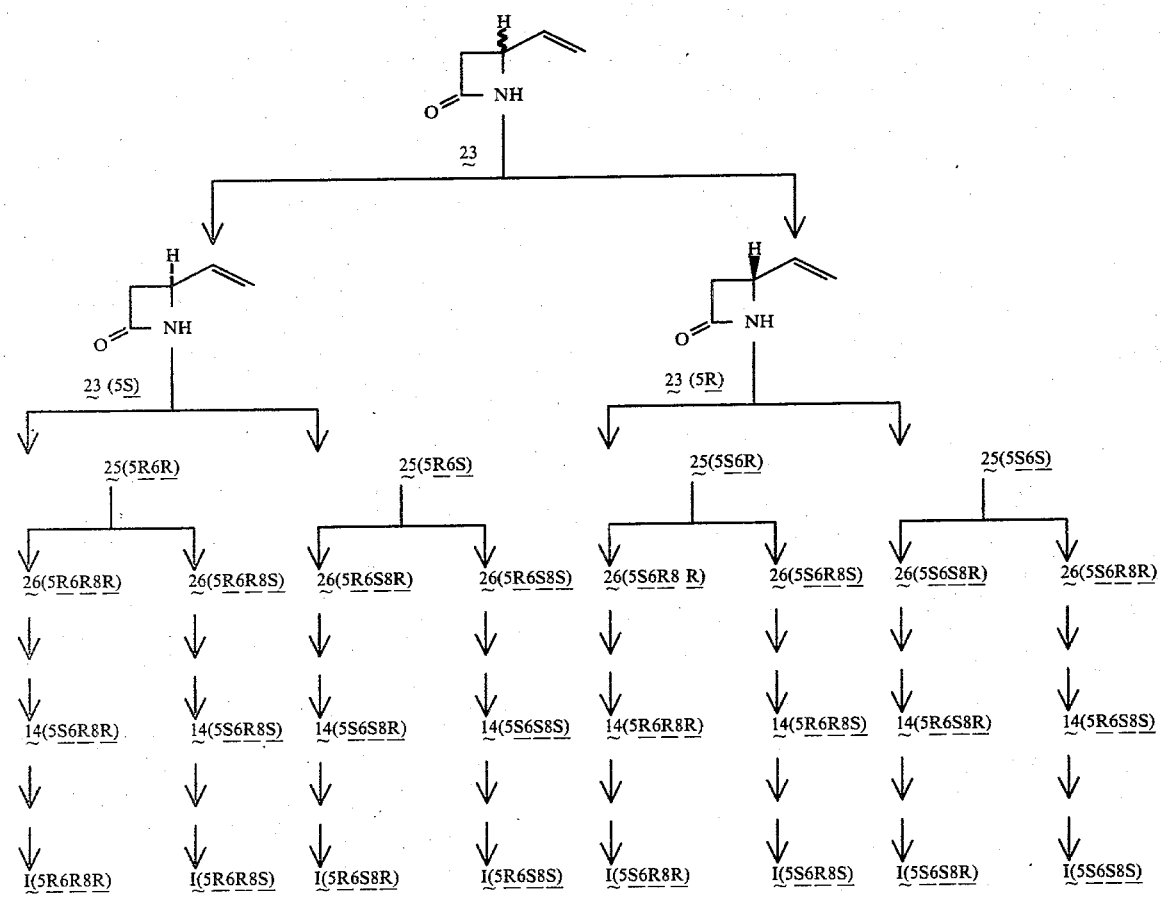

In words relative to the above diagram isomers 23(5S) and 23(5R) are obtained according to known procedures [British Pat. No. 1,273,278]. Silylation, folnolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, tartaric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus the free acid, free base, and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus substilis, Salmonella typhosa, Pseudomonas* and *Bacterium proteus*. The antibacterials of the invention may further be utilized as additives to animal feedingstuffs, for preserving foodstuffs and disinfectants. For example, they may be employed in aqueous compositions in concentrations ranging from 0.01 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, the liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention.

EXAMPLE 1

Preparation of 4-(2-acetoxyvinyl)azetidinone-2-one

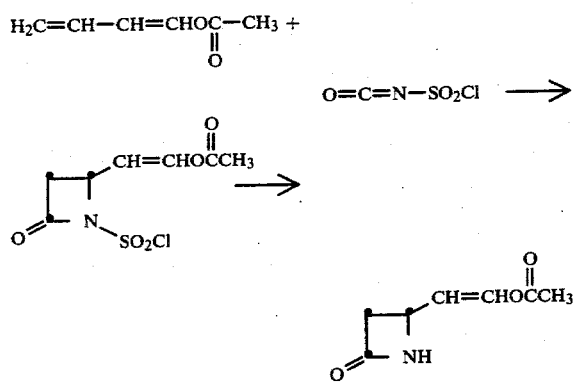

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 2.5 g 1-acetoxybutadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish-orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a $N_2$ stream. The product crystallizes from fractions 4–6, with traces in 3 and 7. Fractions 1–3 contain a yellowish sharp-smelling material which resinifies on standing. Yield: 100 mg as a mixture of the cis and trans isomers.

EXAMPLE 2

Preparation of 4-(2-Acetoxyethyl)-2-Azetidinone

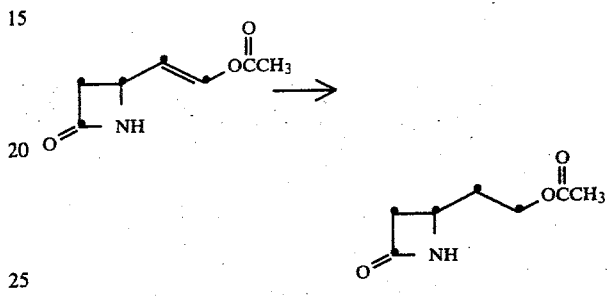

A solution of 4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-(2-acetoxyethyl)-2-azetidinone (10.0 g) as a crystalline solid. Recrystallization from ether affords white crystals: M.P. 44°–7°; ir $(CHCl_3)\mu$ 5.66, 5.74; nmr $(CDCl_3)$ $\tau 3.44$ (broad s, 1, NH), 5.82 (m, 2, $CH_2OCOCH_3$), 6.29 (m, 1, C—4H), 6.87 (½ AB pattern further split in four by C—4H and NH, 1, $J_{gem}=12.8$ Hz, J=4.5H $J_{NH}=1.9$ Hz, 7.38 (½ AB pattern further split in four by C—4H and NH, 1, $J_{gem}=12.8$ Hz, J=2.3 Hz, $J_{NH}=1.0$ Hz), 7.93 and 8.02 (s on m, total 5, $OCOCH_3$ and $CH_2CH_2OCOCH_3$, respectively).

EXAMPLE 3

Preparation of 4-(2-Hydroxyethyl)-2-Azetidinone

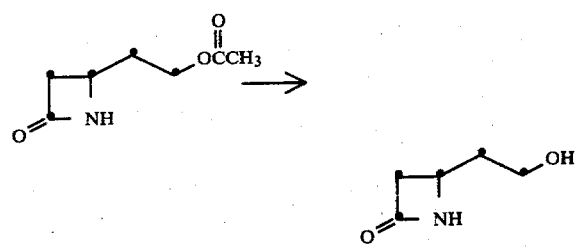

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/$CHCl_3$ to give 1.55 g of the alcohol: m.p. 50°; ir $(CHCl_3)$ $\mu 5.67$; nmr $(CDCl_3)$ $\tau 3.20$ (broad s, 1, NH), 6.24 and 6.28 (m on t, total 3, C—4H and CH$_2$OH respectively), 6.90 (broad s on ½ AB pattern further split in four by C—4H and NH, total 2, OH and C—3H respectively, J$_{gem}$=13.0 Hz, J$_{vic}$=4.2 Hz, J$_{NH}$=1.6 Hz), 7.42 (½ AB pattern further split in four by C—4H and NH, 1, C—3H, J$_{gem}$=13.0 Hz, J$_{vic}$=2.2 Hz, J$_{NH}$=1.1 Hz), 8.16 (m, 2, CH$_2$CH$_2$OH).

EXAMPLE 4

Preparation of 8-Oxo-2,2-dimethyl-3-oxa-1-azabicyclo[4.2.0]octane

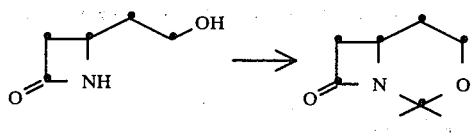

A solution of 4-(2-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]-octane (1.59 g) as a crystalline solid. Recrystallization from ether/hexane gives product of m.p. 60°–1°.

ir (CHCl$_3$) μ: 5.73 (β-lactam)
nmr (CDCl$_3$) τ:
6.02–6.28, m, 2H, C-4 methylene
6.22–6.62, m, 1H, C-6 methine
6.90, dd, 1H, J$_{7,7}$=14 Hz, J$_{6,7}$=4.5 Hz C-7 proton cis to C-6H
7.47, dd, 1H, J$_{7,7}$=14 Hz, J$_{6,7}$=2 Hz C-7 proton trans to C-6H
7.82–8.68, m, 2H, C-5 methylene 8.23, s, 3H  
8.57, s, 3H  } C-2 methyls

EXAMPLE 5

Preparation of 8-oxo-2,2-dimethyl-7α and β-(1-hydroxyethyl)-3-oxa-1-azabicyclo[4.2.0]octane

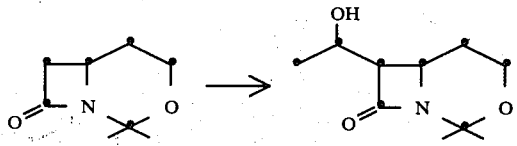

To a solution of 1.1 equivalents of freshly prepared lithium diisopropylamide in anhydrous tetrahydrofuran under a nitrogen atmosphere at −78° is added a solution of 8-oxo-2,2-dimethyl-3-oxa-1-azabicyclo[4.2.0]-octane in anhydrous tetrahydrofuran which has been cooled to −78° C. After two minutes, the resulting lithium enolate is treated with excess acetaldehyde. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2-dimethyl-7α and β-(1-hydroxyethyl)-3-oxa-1-azabicyclo[4.2.0]octane.

Data for 8-oxo-2,2-dimethyl-7β-(1-hydroxyethyl)-3-oxa-1-azabicyclo[4.2.0]octane:
ir (CH$_2$Cl$_2$)μ: 5.72μ (β-lactam)
nmr (CDCl$_3$) τ:
5.53–6.43, m, 4H, C-4 methylene+C-6 methine+C-9 methine
6.90, dd on broad s, 2H, J$_{7,9}$=9 Hz J$_{6,7}$=5.5 Hz, C-7 methine+OH
7.70–8.83, m, 2H, C-5 methylene 8.27, s, 3H  
8.60, s, 3H  } C-2 methyl 8.78, d, 3H, J$_{9,10}$=6.5 Hz, C-10 methyl
Data for 8-oxo-2,2-dimethyl-7α-(1-hydroxyethyl)-3-oxa-1-azabicyclo[4.2.0]octane:
ir (CHCl$_3$) μ: 2.9 broad O—H, 5.73 β-lactam,
nmr (acetone-d$_6$) δ:
4.23–3.33, m, C-9 methine+C-4 methylene+C-6 methine
3.33, broad s, OH 2.83, dd, J = 2Hz, 6Hz  
2.67, dd, J = 2Hz, 8Hz  } C-7 methine 1.93–1.63, m, C-5 methylene 1.63, s  
1.40, s  } C-2 methyls 1.23, d, J=6.5 Hz, C-10 methyl

EXAMPLE 6

Preparation of 8-Oxo-2,2-dimethyl-7α-(1-p-nitrobenzylcarbonyldioxyethyl)-3-oxa-1-azabicyclo[4.2.0]octane

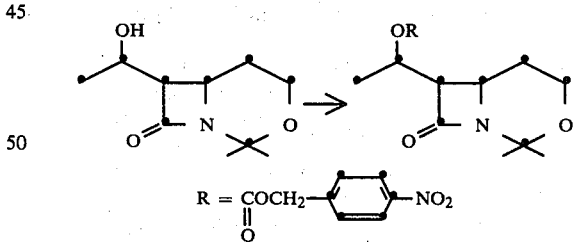

Under anhydrous conditions at 0° C. a solution of 8-oxo-2,2-dimethyl-7α-(1-hydroxyethyl)-3-oxa-1-azabicyclo[4.2.0]octane (60 mg. 0.302 mmole) in 0.6 ml ether is treated with powdered potassium hydroxide (19 mg, 0.332 mmole). After a period of 15 minutes, p-nitrobenzyl chloroformate (65 mg, 0.302 mmole) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure gives 67 mg of a colorless oil. Purification by preparative thick-layer chromatography on silica gel developing with 1:9 ethyl acetate/benzene gives 8-oxo-2,2-dimethyl-7α-(1-p-nitrobenzylcarbonyldioxyethyl)-3-oxa-1-azabicyclo[4.2.0]octane (40 mg) as a mixture of diastereomers.

ir (CH₂Cl₂) μ: 5.68 (β-lactam and carbonate), 6.19 and 6.54 (nitro)

nmr (CDCl₃):
1.67, d, 2H, ArH
2.37, d, 2H, ArH
4.67, s, 2H, ArCH₂
4.67–5.22, m, CH₃CH
5.98–6.25, m, 2H, C-4 methylene
6.25–6.62, m, 1H, C-6 methine
6.75–7.12, m, 1H, C-7 methine
7.75–8.83, m, 2H, C-5 methylene
8.22, s, 3H, C-2 methyl
8.50–8.58, m, 5H, C-2 methyl+CH₃CH The 7β-diastereoisomers or the 7α and β-mixture is obtained in an analogous manner.

EXAMPLE 7

Preparation of Cis and Trans-3-(1-p-nitrobenzylcarbonyldioxyethyl)-4-(2-hydroxyethyl)-2-azetidinone

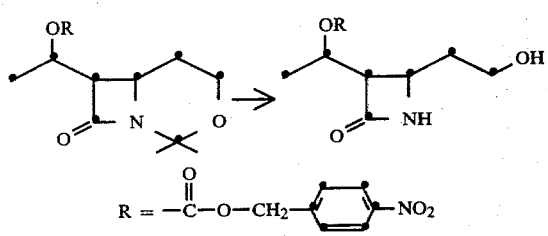

8-Oxo-3-oxa-2,2-dimethyl-7α-(1-p-nitrobenzylcarbonyldioxyethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give trans-3-(1-p-nitrobenzylcarbonyldioxyethyl)-4-(2-hydroxyethyl)-2-azetidinone as a mixture of diastereoisomers.

ir (CH₂Cl₂) μ: 5.67 (β-lactam), 5.72 shoulder, 6.20 and 6.57 (nitro)

nmr (CDCl₃):
1.73, d, 2H, J=8.5 Hz, ArH
2.43, d, 2H, J=8.5 Hz, ArH
3.63, broad s, 1H, NH
4.37–5.13, m, 1H, CH₃CH
4.72, s, 2H, ArCH₂
6.07–6.53, m, 1H, C-4 methine
6.23, t, 2H, J=5.5 Hz, CH₂OH
6.73–6.93, m, 1H, C-3 methine
7.63–8.97, m, 3H, CH₂CH₂OH
8.53, d, J=6.5 Hz, CH₃CH The cis diastereoisomers or the cis-trans mixture is obtained in an analogous manner.

EXAMPLE 8–11

Examples 8, 9, 10, and 11 as alternative to Examples 4, 5 6, and 7 for the preparation of 3-(1-p-nitrobenzylcarbonyldioxyethyl)-4-(2-hydroxyethyl)azetidinone

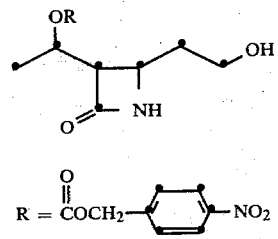

EXAMPLE 8

Preparation of 1-(2-Tetrahydropyranyl)-4-[2-(2-tetrahydropyranyl)oxyethyl]-2-azetidinone

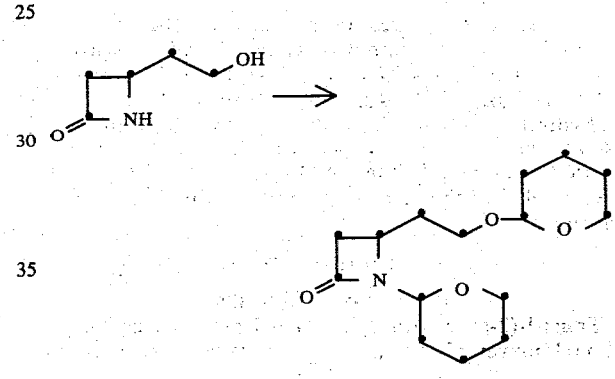

Under nitrogen and at 25° C., a solution of 4-(2-hydroxyethyl)-2-azetidinone (62 mg, 0.539 mmole) in 0.5 ml of anhydrous p-dioxane is treated with 2,3-dihydropyran (0.98 ml, 1.08 mmoles) and p-toluenesulfonic acid monohydrate (19 mg, 0.10 mmole). The resulting solution is stirred for a period of 60 minutes and then partitioned between 10 ml of 0.5 M pH 7 phosphate buffer and 10 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give 216 mg of crude product. Purification by preparative thick-layer chromatography developing with ethyl acetate gives 80 mg of 1-(2-tetrahydropyranyl)-4-[2-(2-tetrahydropyranyl)oxyethyl]-2-azetidinone as an oil.

nmr (CDCl₃) τ:
5.13–5.60, m, OCH
5.83–6.85, m, C-4H+OCH₂

6.95, dd, J = 5Hz and 15 Hz  } C-3 methylene
7.35, dd, J = 3Hz and 15 Hz 7.62–8.95, m, CHCH₂CH₂CH₂CH₂+CHCH₂CH₂O

EXAMPLE 9

Preparation of Cis and
Trans-1-(2-tetrahydropyranyl)-3-(1-hydroxyethyl)-4-[2-(2-tetrahydropyranyl)oxyethyl]-2-azetidinone

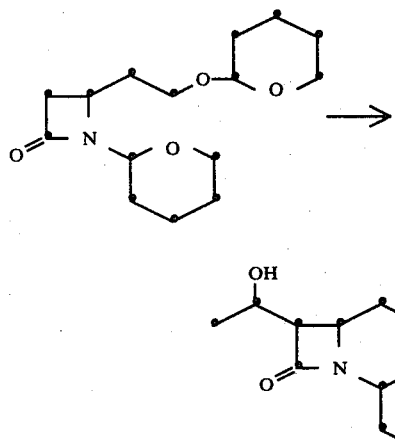

Following the procedure described for the preparation of 8-oxo-2,2-dimethyl-7α and β-(1-hydroxyethyl)-3-oxa-1-azabicyclo[4.2.0]octane from 8-oxo-2,2-dimethyl-3-oxa-1-azabicyclo[4.2.0]octane and using 1-(2-tetrahydropyranyl)-4-[2-(2-tetrahydropyranyl)oxyethyl]-2-azetidinone one obtains a diastereomeric mixture of both cis and trans-1-(2-tetrahydropyranyl)-3-(1-hydroxyethyl)-4-[2-(2-tetrahydropyranyl)-oxyethyl]-2-azetidinone.

EXAMPLE 10

Preparation of Cis and
Trans-1-(2-tetrahydropyranyl)-3-(1-p-nitrobenzylcarbonyldioxyethyl)-4-[2-(2-tetrahydropyranyl)oxyethyl]-2-azetidinone

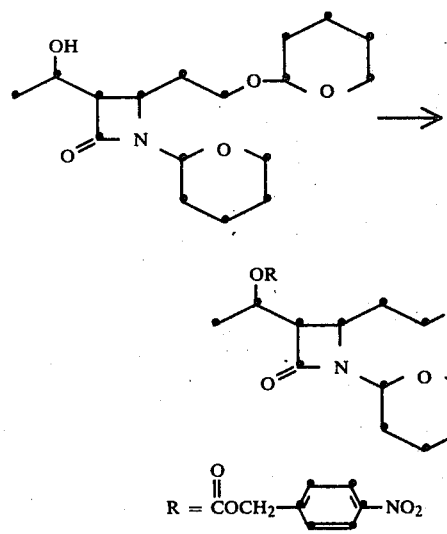

Following the procedure described for the preparation of 8-oxo-2,2-dimethyl-7α-(1-p-nitrobenzylcarbonyldioxyethyl)-3-oxa-1-azabicyclo[4.2.0]octane from 8-oxo-2,2-dimethyl-7α-(1-hydroxyethyl)-3-oxa-1-azabicyclo[4.2.0]octane and using trans-1-(2-tetrahydropyranyl)-3-(1-hydroxyethyl)-4-[2-(2-tetrahydropyranyl)oxyethyl]-2-azetidinone there is obtained trans-1-(2-tetrahydropyranyl)-3-(1-p-nitrobenzylcarbonyldioxyethyl)-4-[2-(2-tetrahydropyranyl)oxyethyl]-2-azetidinone. The cis diastereoisomers are obtained in an analogous manner.

EXAMPLE 11

Preparation of Cis and
Trans-3-(1-p-nitrobenzylcarbonyldioxyethyl)-4-(2-hydroxyethyl)-2-azetidinone

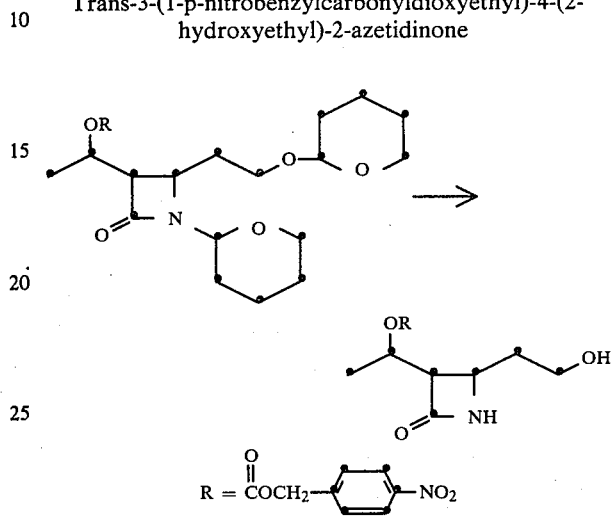

A solution of trans-1-(2-tetrahydropyranyl)-3-(1-p-nitrobenzylcarbonyldioxyethyl)-4-[2-(2-tetrahydropyranyl)oxyethyl]-2-azetidinone in methanol at 25° C. is treated with 0.1 molar equivalent of p-toluenesulfonic acid monohydrate. The solution is stirred for a period of 2 hours and then neutralized with 1 M pH 7 phosphate buffer. The product is extracted into ethyl acetate. The ethyl acetate solution is washed with brine, dried over magnesium sulfate and filtered. The filtrate is evaporated under reduced pressure to give trans-3-(1-p-nitrobenzylcarbonyldioxyethyl)-4-(2-hydroxyethyl)-2-azetidinone. The cis diastereoisomers are obtained in an analogous manner.

EXAMPLE 12

Preparation of (5R,6S,8S)- and (5S,6R,8R)-3-(2-aminoethylthio)-6-(1-hydroxyethyl)-7-oxo-1-azabicyclo[3.2.0]hept-2-ene-2-carboxylic acid.

STEP A

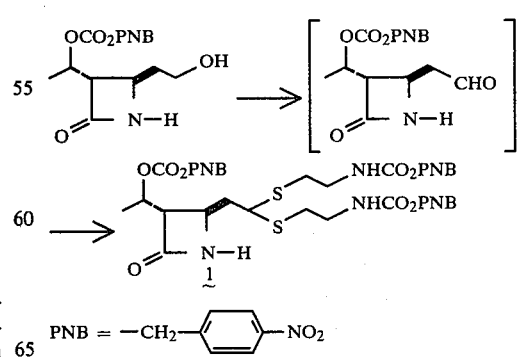

To 6.75 ml anhydrous pyridine (mw=79; ρ=0.982; 83.9 mmole) in 350 ml anhydrous acetonitrile is added 4.05 g anhydrous powdered chromium trioxide (mw=100; 40.5 mmole). After stirring at room temperature (25° C.) for 30 minutes, 9.6 g dried Supercell is added and stirring is continued for 5 additional minutes. A solution of 3.21 g trans-3-(1-p-nitrobenzlcarbonyldioxyethyl)-4-(2-hydroxyethyl)-2-azetidinone (mw=338; 9.5 mmole) in 30 ml anhydrous acetonitrile is added all at once. The reaction mixture is stirred under anhydrous conditions at room temperature (25° C.) for one hour. Addition of 9.6 g NaHSO₃ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate ~600 ml).

The filtrate is concentrated under a N₂ stream to 130 ml total volume.

To this solution containing crude aldehyde at 0° C. under N₂ is added 9.64 g p-nitrobenzyloxycarbonylaminoethanethiol (mw=256; 37.7 mmole) as prepared below (Example 12, Step B). To the stirred reaction mixture is added 8.0 ml boron trifluoride etherate (mw=142; ρ=1.125; 63.4 mmole). After 1.5 hours at 0° C., the reaction mixture is poured into a stirred ice-cold mixture of 69 g K₂HPO₄—500 ml H₂O and 700 ml ethyl acetate (EA). The layers are separated, and the aqueous one is saturated with NaCl and re-extracted with additional EA. The combined organic layers are washed twice with brine, dried over anhydrous MgSO₄ and filtered. The filtrate is concentrated under a N₂ stream and then pumped on high vacuum to give 14.5 g crude 1.

The material is chromatographed on 450 g silica gel (column height=48 cm; diameter=5.5 cm) packed and applied in CHCl₃ and eluted with increasing percentages of MeOH in CHCl₃ (0-4% MeOH/CHCl₃). Those fractions containing the desired product are combined, concentrated under a N₂ stream; and pumped on high vacuum to give 5.09 g of 1 (65% yield).

NMR (d₆-acetone):
8.17-7.47 (aromatic protons), 7.25 (active hydrogen), 6.69 (active hydrogen), 5.40-4.97 (—CH₂—φ—p—NO₂'s & CH₃—C$\underline{H}$—O), 4.12

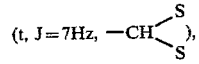
(t, J=7Hz, —CH$\overset{S}{\underset{S}{\diagup}}$), 3.80 (m, C₄—H), 3.35 (m, —CH₂—NH— & C₃—H), 2.82 (m, —S—CH₂—), 2.15

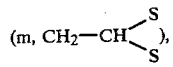
(m, CH₂—CH$\overset{S}{\underset{S}{\diagup}}$), 1.42 (d, J=6.5 Hz, C$\underline{H}$₃—CH—O) in ppm downfield from TMS.

IR (CHCl₃ solution) carbonyls ~1770 cm⁻¹ & ~1725 cm⁻¹

STEP B

Preparation of p-Nitrobenzyloxycarbonylaminoethanethiol

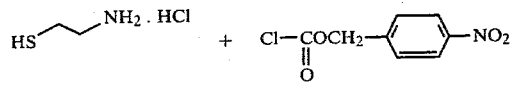

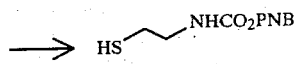

To 600 ml diethyl ether(Et₂O)-75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g p-nitrobenzloxycarbonylaminoethanethiol (65% yield).

NMR (CDCl₃):
8.18 (d, J=8 Hz, aromatic protons ortho to nitro), 7.47 (d, J=8 Hz, aromatic protons meta to nitro), 5.27 (—N$\underline{H}$—), 5.20 (s, —C$\underline{H}$₂—φ—pNO₂), 3.40 (m, —C$\underline{H}$₂—NH—), 2.67 (m, —C$\underline{H}$₂—SH), 1.35 (t, J=8.5 Hz, —S$\underline{H}$) in ppm downfield from TMS.

IR (CHCl₃ solution) carbonyl—~1725 cm⁻¹

M.S.—molecular ion-256, (M-47) at 209, (M-136) at 120, ⁺CH₂φpNO₂ at 136.

STEP C

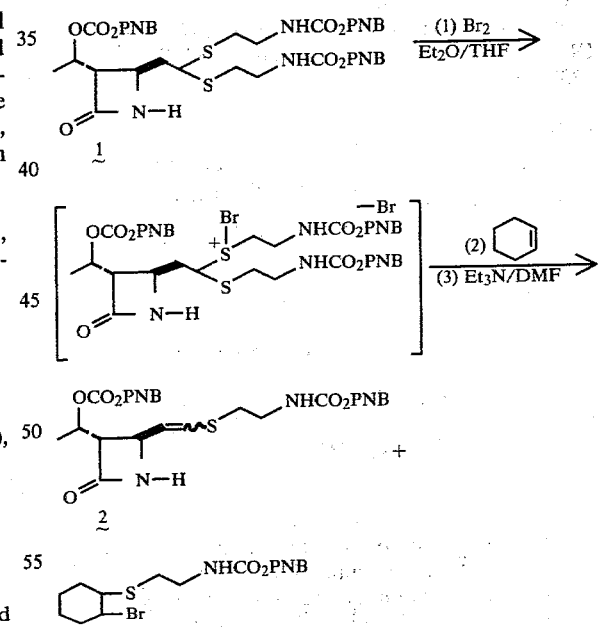

To 14.2 ml pentane (dried over 4 A Linde molecular sieves) is added 0.5 ml Br₂ (mw=160; 9.75 mmole). To 5 g of 1 (mw=830; 6.02 mmole) in 58 ml tetrahydrofuran(THF) (freshly distilled from lithium aluminum hydride)(LAH) and 65 ml Et₂O (dried over 3 A 1/16" Linde molecular sieves) at 0° C. under N₂ with stirring is added dropwise 10 ml of the above 0.66 M Br₂ solution (6.6 mmole). After 10 minutes at 0° C., 0.67 ml cyclohexene (mw=82; ρ=0.81; 6.6 mmole) is added. After 5 minutes at 0° C., 1.7 ml triethylamine (mw=101; ρ=0.729; 12.3 mmole) is added immediately followed by 40 ml ice-cold dimethylformamide(DMF) (distilled from anhydrous CaSO$_4$ at 40 mm and stored over 4 A Linde molecular sieves). The ice bath is removed, and stirring is continued for 2¼ hours at room temperature. The reaction mixture is poured into a stirred ice-cold mixture of 12.6 ml 1MKH$_2$PO$_4$ 160 ml H$_2$O—500 ml (EA). After separation of the layers, the aqueous one is saturated with sodium chloride and reextracted with EA. The combined organic layers are extracted once with brine, dried over anhydrous MgSO$_4$, filtered and concentrated under a N$_2$ stream followed by pumping under high vacuum to provide crude 2.

The material is chromatographed on 250 g silica gel (height=45 cm; diameter=4.5 cm) packed and applied in CHCl$_3$ and eluted with increasing percentages of MeOH in CHCl$_3$ (0–3% MeOH/CHCl$_3$). Those fractions containing clean product are combined, concentrated under a N$_2$ stream, and pumped on high vacuum to give 2 g of 2. Contaminated fractions are rechromatographed on silica gel using increasing percentages of EA in CHCl$_3$ (0–25% EA/CHCl$_3$) to give an additional 0.645 g of 2 (total yield=77%).

NMR (d$_6$-acetone):
 8.40–7.54 (aromatic protons), 7.30 (active hydrogen), 6.72 (active hydrogen), 6.44 (d, J=15 Hz, —CH═CH—S— (trans)), 6.34 (d, J=9 Hz, —CH═CH—S— (cis)), 5.77 (dd, J=15,7 Hz, —CH═CH—S— (trans)), 5.74 (dd, J=9, 8 Hz, —CH═CH—S-(cis)), 5.44–4.92 (—CH$_2$—φ—p—NO$_2$'s & CH$_3$—CH—O), 4.34 (dd, J=8,3 Hz, C$_4$—H of cis-thioenolether), 4.09(dd, J=7, 3 Hz, C$_4$—H of trans-thioenolether), 3.35 (m, —CH$_2$—NH & C$_3$—H's), 2.90 (m, —S—CH$_2$—), 1.42 (d, J=6.5 Hz, CH$_3$—CH—O) in ppm downfield from TMS.
IR (CHCl$_3$ solution): carbonyls—~1767 cm$^{-1}$ & ~1730 cm$^{-1}$.

STEP D

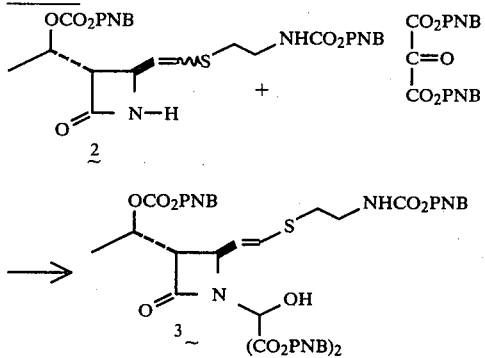

To a stirred solution of 2.48 g di(p-nitrobenzyl) ketomalonate (from Example 12, Step E) (mw=388; 6.39 mmole) in 400 ml hot anhydrous toluene is added a solution of 2.52 g of 2 (mw=574; 4.39 mmole) in 20 ml THF (distilled from LAH) and 40 ml anhydrous toluene. After some of the solvent is boiled off, additional anhydrous toluene is added, and the azeodrying process is repeated three times. The solution is then refluxed under N$_2$ for 30 minutes. Additional toluene is then allowed to boil off yet the volume is not allowed to diminish so much that precipitation occurs. Total heating time is approximately 2½ hours. The clear yellow reaction mixture is removed from the oil bath and placed under a stream of N$_2$ which instantaneously causes clouding. After concentration to a yellow oil, the residue is dissolved in CH$_2$Cl$_2$, dried over anhydrous MgSO$_4$, filtered, and concentrated under a N$_2$ stream to give crude 3.

The material is chromatographed on 250 g silica gel packed and applied in CHCl$_3$ (height=43 cm; diameter=4.5 cm). Elution with 500 ml 0.5% MeOH/CHCl$_3$ is followed by continued elution with 1% MeOH/CHCl$_3$ for the remainder of the chromatography. After the emergence of excess reagent, those fractions containing pure 3 are combined, concentrated under a N$_2$ stream and then on high vacuum to give 1.22 g of 3.

Later fractions containing 3 and the corresponding cis thioenol ether are re-chromatographed on silica gel to give an additional 0.5 g of 3 (total yield=40%).

NMR (d$_6$-acetone):
 8.28–7.45 (aromatic protons), 6.65 (br.s., active hydrogen), 6.48 (d, J=15 Hz, —CH═CH—S—), 5.78 (dd, J=15, 8 Hz, —CH═CH—S—), 5.45–5.07 (—CH$_2$—φ—pNO$_2$'s & CH$_3$—CH—O), 4.65 (dd, J=8, 3 Hz, C$_4$—H), 3.40 (m, —CH$_2$—NH— & C$_3$—H), 2.88 (m, —S—CH$_2$—), 1.42 (d, J=7 Hz, CH$_3$—CH—O) in ppm downfield IR (CHCl$_3$ solution): carbonyls—~1758 cm$^{-1}$, shoulder at ~1725 cm$^{-1}$ The cis thioenol ether or mixtures of cis and trans thioenol ethers can be carried through the subsequent steps to yield additional 9.

STEP E

Preparation of di-p-Nitrobenzyl Ketomalonate

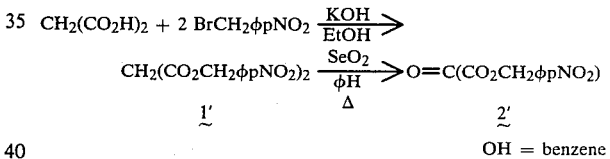

φH = benzene

A mixture of 100 g p-nitrobenzyl bromide (0.46 mole), 28.6 g malonic acid (0.275 mole) and 750 ml ethanol-(EtOH) is stirred and warmed on the steam bath until solution is achieved. A solution of 33 g KOH (>85% purity; ~0.6 mole) in 200 ml of water is added carefully with swirling. An additional 200 ml of water is added, and the two-phase system is refluxed for 1.8 hours. The lighter color homogeneous solution is cooled in ice for 1 hour and the crude product isolated by filtration, washed twice with a minimum of cold EtOH, and dried by pulling dry N$_2$ through the cake; 33.7 g of solid is obtained. If, during the refluxing stage the reaction mixture is slowly concentrated on ca. half volume by allowing refluxing solvent to distill off, the crude product yield rises to 77 g. The material is recrystallized from methanol to give pure di-p-nitrobenzyl malonate 1'.

A mixture of 23.4 of 1', 10 g SeO$_2$, and 30–40 ml of xylene is stirred in a flask immersed in an oil bath. The bath temperature is raised over 1 hour to 130°–135°. A gradual darkening of the reaction mixture is noted, and after a total of 4 hours at 130°–135°, most of the insoluble residue is black Se°. The mixture is cooled, MgSO$_4$ is added to remove the water, and Celite is added to aid in filtration. The mixture is filtered through Celite and the cake washed with xylene and a small portion of EtOAc. Final volume: 60 ml. A 100 g column of Baker Silica Gel is prepared in benzene and 10 ml of filtrate applied, then eluted with increasing amounts of EtOAc in benzene, 500 ml fractions being collected. After one 2% ethyl acetate (EtOAc)/φH, and two 10% EtOAc/φH fractions, the third 10% and first 20% EtOAc/φH provide the bulk of the product (~1.6 g from 10 ml filtrate) as judged by tlc (20% EtOAc/CHCl₃; silica gel GF). Recrystallization from benzene, (1 g in ca. 50 ml concentrated to ~⅓ volume and "spiked" with 1 ml of H₂O saturated benzene) provides 0.24 g 2'; mp(117) 121°–122°.

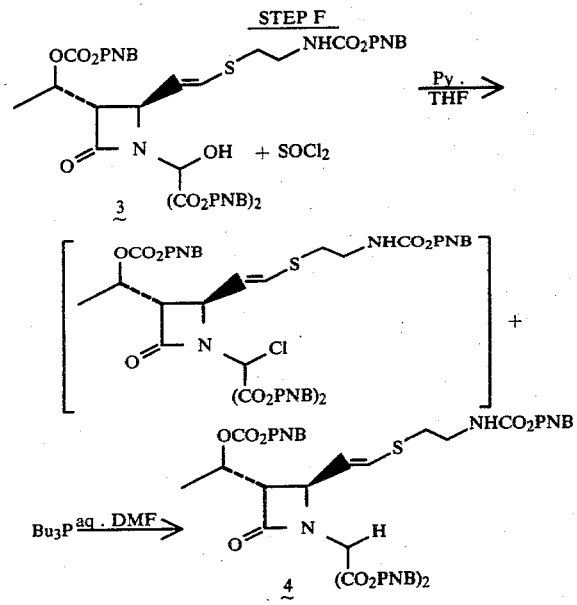

STEP F

A solution of 1.468 g of 3 (mw=962; 1.53 mmole) in CH₂Cl₂ is dried over anhydrous MgSO₄, filtered, concentrated under a N₂ stream, and dried further under high vacuum just prior to the following reaction. To a solution of 3 in 24 ml THF (freshly distilled from LAH) at −20° C. is added 0.206 ml anhydrous pyridine (mw=79; ρ=0.982; 2.56 mmole). With stirring under N₂, 294 mg of freshly distilled thionyl chloride (mw=119; 2.47 mmole) in 5 ml THF is added dropwise. The reaction mixture is stirred for 10 minutes at −20° C., then ½ hour at 0° C. and finally 1 hour at 25° C. The pyridine hydrochloride is filtered under N₂ and washed with 20 ml THF. The filtrate is concentrated under N₂ stream followed by pumping on high vacuum. The resulting yellow foam is swirled in 25 ml anhydrous THF, and a small amount of orange-red insoluble material is filtered off under N₂. The filtrate is re-concentrated as above to a yellow foam.

To this freshly prepared chloro compound is added with stirring a freshly shaken suspension of 678 mg tributylphosphine (mw=202; 3.36 mmole) in 36.5 ml 9:1 DMF—H₂O followed by 294 mg K₂HPO₄ (mw=174; 1.69 mmole). The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous MgSO₄, filtered and concentrated under a N₂ stream followed by pumping on high vacuum to give crude 4.

The material is chromatographed on 100 g silica gel (height=28.5 cm; d=4 cm) packed and applied in CHCl₃ and eluted with 0.5% MeOH in CHCl₃. Those fractions containing clean product are combined, concentrated under a N₂ stream and then on high vacuum to give 0.786 g of 4. Contaminated fractions are re-chromatographed on silica gel thin layer plates (eluant=50% acetone/hexane; extraction of desired u.v. band with CHCl₃ and EA) to provide 0.203 g additional 4 (total yield=64%).

NMR (d₆-acetone): 8.30–7.50 (aromatic protons), 6.68 (active hydrogen), 6.53 (d, J=15 Hz, —CH=CH—S), 5.68(dd, J=15, 9 Hz, —CH=CH—S), 5.45–5.03 (—CH₂—φ—pNO₂'s, CH₃—CH—O, & —CH(—CO₂CH₂φ—pNO₂)₂), 4.53(dd, J=9, 2.5 Hz, C₄—H), 3.41 (m, —CH₂—NH— & C₃—H), 2.85(m, —S—CH₂—), 1.41(d, J=7 Hz, CH₃—CH—O) in ppm downfield from TMS.

IR (CHCl₃ solution): carbonyls ~1750 cm⁻¹, shoulders at ~1725 cm⁻¹ & ~1775 cm⁻¹.

STEP G

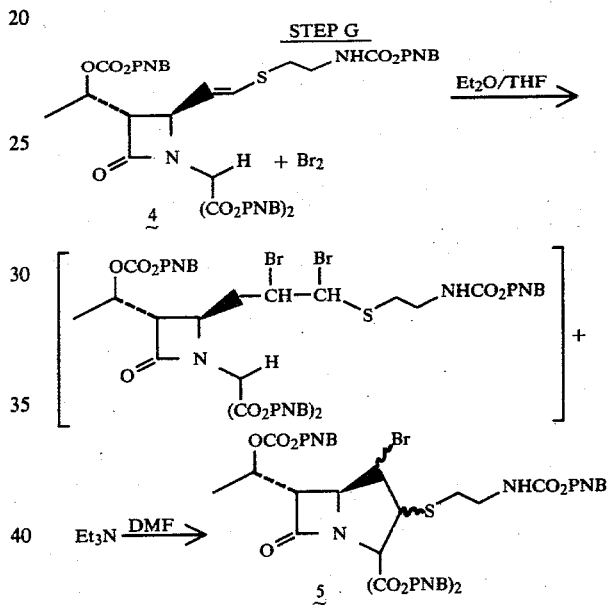

To 8.5 ml pentane (dried over 4 A Linde molecular sieves) is added 0.2 ml Br₂ (mw=160; 3.9 mmole). To 0.706 g of 4 (mw=946; 0.746 mmole) in 18 ml THF (freshly distilled from LAH) and 5.7 ml Et₂O (dried over 3 A 1/16" Linde molecular sieves) at 0° C. under N₂ with stirring is added dropwise 1.8 ml of the above 0.45 M Br₂ solution (0.81 mmole). After 15 minutes at 0° C., 0.42 ml triethyl amine (mw=101; ρ=0.729; 3.03 mmole) is added immediately followed by 10.5 ml ice-cold DMF (distilled from CaSO₄ at 40 mm and stored over 4 A Linde molecular sieves). The ice-bath is removed, and stirring at room temperature is continued for 2 hours. The reaction mixture is poured into a stirred ice-cold mixture of 3.1 ml 1 M KH₂PO₄—70 ml H₂O—100 ml EA. The layers are separated, and the aqueous one is saturated with NaCl and re-extracted with EA. The combined organic layers are washed once with brine, dried over anhydrous MgSO₄, and filtered. The filtrate is concentrated under a N₂ stream and then pumped on high vacuum to give crude 5.

The material is chromatographed on 60 g silica gel (diameter=2.8 cm) packed and applied in CHCl₃ and is eluted with 100 ml-2% EA/CHCl₃; 100 ml-4% EA/CHCl₃ and then 5% EA/CHCl₃ for the remainder of the chromatography. The fractions containing pure 5 are combined, concentrated under a N₂ stream, and pumped on high vacuum to give 0.385 g of 5 (50% yield).

NMR (d₆-acetone):
8.32–7.45 (aromatic protons), 6.55 (active hydrogen), 5.45–5.14 (—C$\underline{H}$₂—ϕ—pNO₂'s & CH₃—C$\underline{H}$—O), 5.07 (dd, J=6, 5 Hz, —C$\underline{H}$Br), 4.49 (d, J=6 Hz, —C$\underline{H}$S—), 4.29(dd, J=5, 3 Hz,C₅—H), 3.85(dd, J=4.5, 3 Hz, C₆—H), 3.42(m, —C$\underline{H}$₂—NH—) 2.89 (—S—C$\underline{H}$₂—), 1.45 (d, J=6.5 Hz, C$\underline{H}$₃—CH—O) in ppm downfield from TMS.

IR (CHCl₃ solution): β-lactam—~1783 cm⁻¹, carbonyls ~1742 cm⁻¹.

STEP H

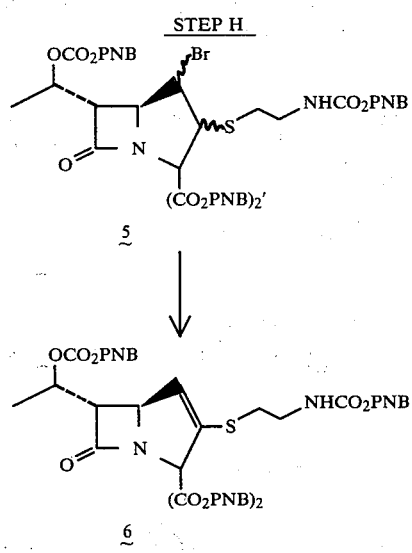

To 29 mg anhydrous silver fluoride (mw=127; 0.23 mmole) is added a solution of 146 mg of 5 (mw=1024; 0.14 mmole) in 3.5 ml anhydrous pyridine. The stoppered reaction mixture is stirred at room temperature in the dark for one hour and then poured into 20 ml cold water—30 ml EA. After separation of the layers, the aqueous one is extracted two times with EA and one time with CHCl₃. Each organic layer is extracted one time with H₂O and one time with brine. The combined organic layers are dried over anhydrous MgSO₄, filtered, and concentrated under a N₂ stream followed by pumping on high vacuum to give crude 6.

Preparative thin layer chromatography (eluant=40% acetone/hexane; repeated extraction of desired u.v. band with a large volume of CHCl₃) yields slightly contaminated 6. Re-chromatographing on silica using EA in CHCl₃ as an eluting system gives 95 mg pure 6 (70% yield).

NMR (CDCl₃):
8.32–7.35 (aromatic protons), 6.18 (br.d, J≅1.5 Hz, vinyl proton), 5.50–5.05 (—CH₂—ϕ—pNO₂'s & CH₃—CH—O), 4.57 (dd, J=3,~1.5 Hz, C₅—H), 3.47 (m, —CH₂—NH— & C₆—H), 3.03 (m, —S—CH₂—), 1.47 (d, J=6.5 Hz, C$\underline{H}$₃—CH—O) in ppm downfield from TMS.

IR (CHCl₃ solution): β-lactam—~1790 cm⁻¹, carbonyls—~1745 cm⁻¹.

STEP I

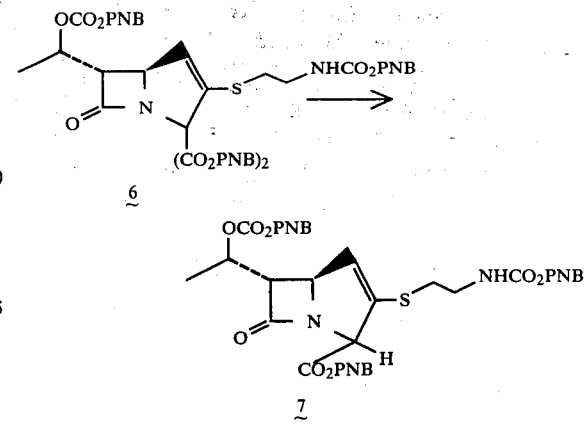

A solution of 77 mg of 6 (mw=944; 0.082 mmole) in 0.9 ml S-collidine (distilled from powdered KOH~30 mm pressure) is added to 13.4 mg anhydrous LiI (dried for few hours at 100° C. over P₂O₅ under vacuum) (mw=134; 0.1 mmole). With stirring under N₂, the reaction mixture is heated in an oil bath at 120° C. After a total of 30 minutes, the reaction mixture is cooled to 25° C., diluted with CH₂Cl₂, and transferred to a round bottom flask for concentration under a N₂ stream and then on high vacuum. Partitioning the residue between EA-H₂O and 1 ml 1 M KH₂PO₄ is followed by extraction of the aqueous layer two additional times with EA and one time with CHCl₃. Each organic layer is then backwashed with brine. The combined organic layers are dried over anhydrous MgSO₄, filtered, concentrated under a N₂ stream and then on high vacuum to give crude 7.

Preparative thin layer chromatography on silica gel (plate is eluted two times with 40% acetone/hexane; repeated extraction of desired u.v. bands with large volume of CHCl₃) yields 18 mg of starting material and 28 mg of 7 (44% yield).

NMR (CDCl₃):
8.30–7.50 (aromatic protons), 6.00 (m, vinyl proton), 5.38–5.10 (—C$\underline{H}$₂—ϕ—pNO₂'s, CH₃—C$\underline{H}$—O, & C₂—H), 4.53 (m, C₅—H), 3.44 (m, —CH₂—NH—), 3.35(dd, J=5, 3 Hz, C₆—H), 3.00 (m, —S—C$\underline{H}$₂—), 1.50 (d, J=6.5 Hz, C$\underline{H}$₃—CH—O) in ppm downfield from TMS.

IR (CHCl₃ solution): β-lactam—~1783 cm⁻¹, carbonyls—~1750 cm⁻¹ & ~1735 cm⁻¹.

STEP J

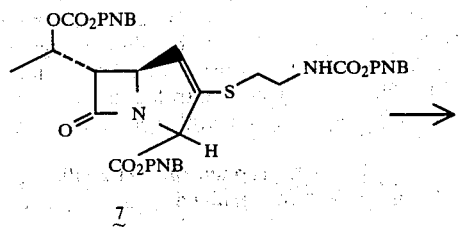

-continued
STEP J

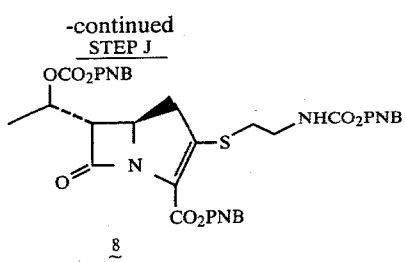

To 49 mg of 7 (mw=765; 0.064 mmole) in 0.7 ml DMSO (distilled from CaH$_2$ at 8 mm and stored over 4A Linde molecular sieves) is added 100 μl diisopropylamine (distilled from NaH under N$_2$ and stored over 4A Linde molecular sieves) (mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a column of silica gel (packed, applied, and eluted with EA) to remove residual DMSO. After concentration under a N$_2$ stream of all fractions having u.v. absorbance, the material is chromatographed on a thin layer silica gel plate (eluant=50% EA/CHCl$_3$; repeated extraction of desired u.v. bands with a large volume of chloroform). The starting material band yields 35 mg. The product band yields 6 mg of 8. Starting material is re-submitted to the reaction conditions and isolation procedure two more times to yield 9 mg additional 8 (total yield=30%).

NMR (CDCl$_3$): 8.27–7.47 (aromatic protons), 5.53–5.13 (—C$\underline{H}_2$—ϕ—pNO$_2$'s & CH$_3$C$\underline{H}$—O—), 4.17 (m, C$_5$—H), 3.50 (dd, J=5,3 Hz, C$_6$—H), 3.43 (m, —C$\underline{H}_2$—NH—) 3.03 (m, —S—C$\underline{H}_2$— & C$_4$—H's), 1.50 (d, J=6 Hz, C$\underline{H}_3$—CH—O), in ppm downfield from TMS.

IR (CHCl$_3$ solution): β-lactam—~1783 cm$^{-1}$, carbonyls—~1743 cm$^{-1}$ & ~1725 cm$^{-1}$.

STEP K

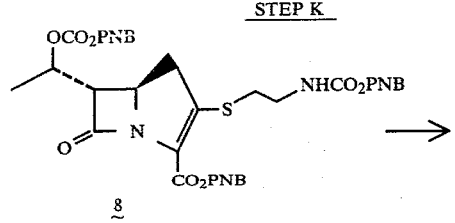

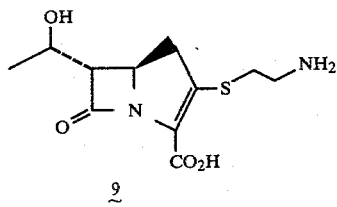

To 5.2 mg 8 is added 0.60 ml dioxane, 0.05 ml ethanol, 0.35 ml deionized water and 0.01 ml of 1.0 M K$_2$HPO$_4$. To the resultant clear solution is added 5 mg of 10% Pd/C. The suspension is flushed with N$_2$, then 5–6 times alternately with 50 psi H$_2$ and vacuum. Finally, it is shaken under a 50 psi H$_2$ atmosphere for 30–40 min. After centrifugation, the Pd/C is washed and centrifuged 2–3X with 0.5 ml portions of deionized water. The combined centrifugates are extracted 5×1–2 ml ether. Residual ether is removed under vacuum and the aqueous solution applied to an XAD-2 column (20×140 mm). Fractions of 100 drops (6–7 ml) are collected, with continuous UV monitoring, by elution with deionized water. Emergence of strongly UV absorbing material begins around fractions 3–5 and is usually complete by fractions 25–30. Early fractions are examined by UV to exclude those few deemed too strongly absorbing in the 270–280 mμ region. The remaining fractions are combined and lyophilized. The residue is evaluated by dissolving in 10.0 ml of deionized water and measuring the UV absorbtion at 298 mμ indicating a 10–30% yield of desired product. The nmr spectrum in D$_2$O shows, amongst other peaks, a multiplet with prominent peaks at 4.24, 4.18, 4.13 and 4.06δ(C$_5$ and C$_8$ protons), a doublet of doublets at 3.49δ(C$_6$-proton J$_{5-6}$=2.5 Hz; J$_{6-8}$=4.9 Hz), two strong broad peaks at 3.20 and 3.14δ and a broader multiplet between 2.8 and 3.0δ due to the three sets of methylene protons, and a sharp doublet at 1.31δ(J$_{8-9}$=6.4 Hz) for the side chain methyl.

STEP L

Resolution of the Racemic Mixture

The racemic mixture comprising the desired (5R6S8S)- and (5S6R8R)-3-(2-aminoethylthio)-6-(1-hydroxyethyl)-7-oxo-1-azabicyclo[3.2.0]hept-2-ene-2-carboxylic acid in 20% ethanolic water is treated with an equimolar quantity of threo-S-p-nitrophenyl-2-aminopropane-1,3-diol, warmed to 50°, and allowed to cool. When crystallization appears complete, the mother liquors are carefully pipetted away and the crystals washed on a filter with the minimum amount of ice-cold 20% ethanolic water. The combined filtrates and mother liquors upon standing in the refrigerator for 18 hrs afford the salt of the other enantiomer which is isolated by filtration and washed with a minimum of ice cold 20% ethanolic water. The salts are separately taken up in water, and passed through an XAD-2 column, eluting with water, and monitoring the eluate by U.V. The aromatic amine is retarded by the column, providing the desired isomer in the eluate, which upon evaporation yields, respectively, the (5R,6S,8S) and (5S,6R,8R) isomers.

EXAMPLE 13

Preparation of (5R,6R,8R)- and (5S,6S,8S)-3-(2-aminoethylthio)-6-(1-hgydroxyethyl)-7-oxo-1-azabicyclo[3.2.0]hept-2-ene-2-carboxylic acid

Step A

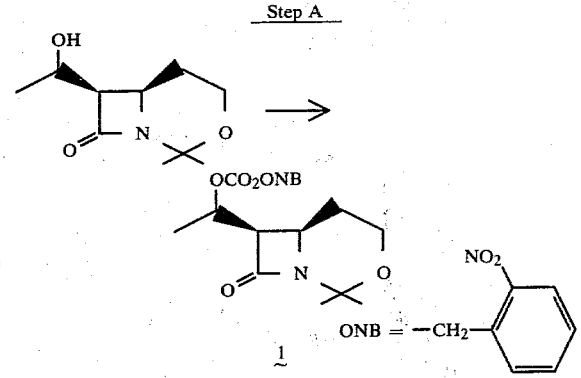

To a solution of 3.7 g of (6R,7R,9R) and (6S,7S,9S)-8-oxo-2,2-dimethyl-7-(1-hydroxyethyl)-3-oxa-1-azabicyclo[4.2.0]-octane (mw=199, 18.6 mmole) and 8.03 g o-nitrobenzylchloroformate (mw=216; 37 mmole) in 80 ml sieve-dried CH₂Cl₂ at 0° C. under N₂ with stirring is added 4.54 g of 4-dimethylaminopryidine (mw=122; 37 mmole). The cooling bath is removed, and the reaction mixture is stirred under N₂ for 2½ hours. An additional 80 ml of CH₂Cl₂ is added, and the reaction mixture is washed successively with cold 0.25 N HCl, water, cold 0.25 N HCl, water (3 times) and brine. After drying over anhydrous MgSO₄, filtration and concentration in vacuo of the CH₂Cl₂ layer, 8.8 g of crude 1 is obtained. Chromatography on 340 g silica gel (eluting with 30% EA/CH₂Cl₂) yields 5.4 g of 1.

Step B

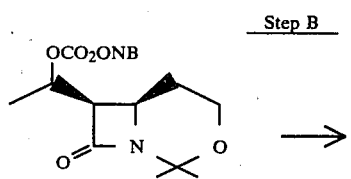

1

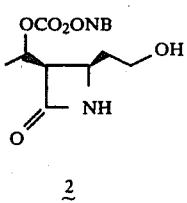

2

Using the method of Example 7 only substituting 1 from Example 13, Step A for 8-oxo-3-oxa-2,2-dimethyl-7α-(1-p-nitrobenzylcarbonyldioxyethyl)-1-azabicyclo[4.2.0]octane, 2 is obtained.

Steps C through K

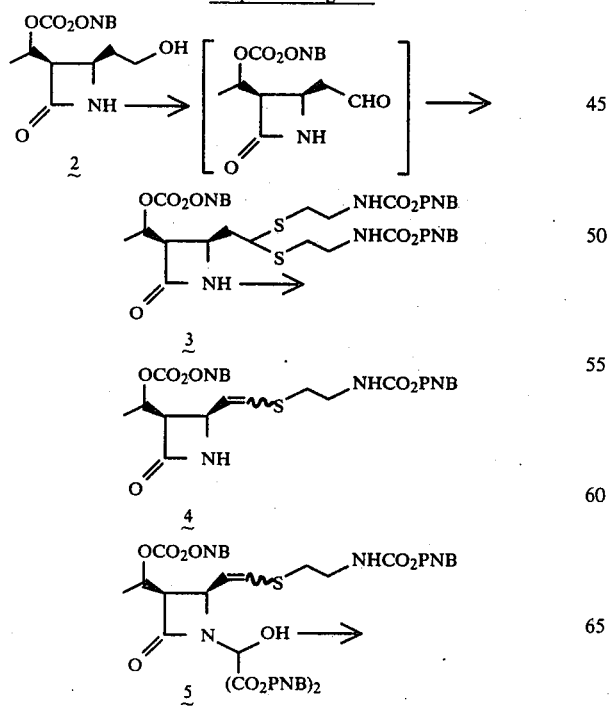

-continued
Steps C through K

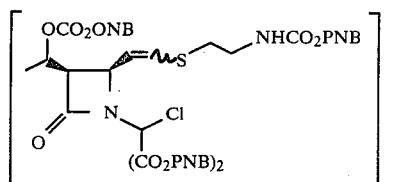

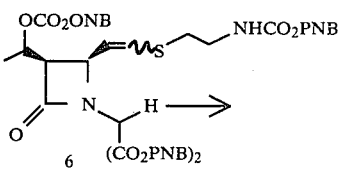

6

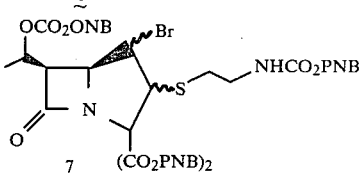

7

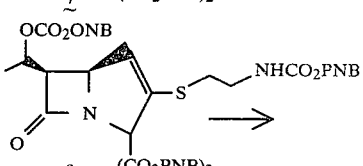

8

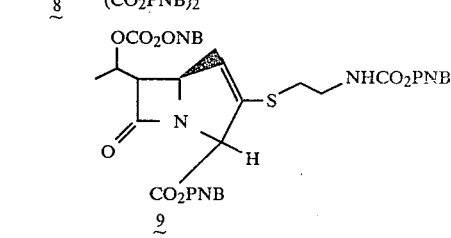

9

Using the methods of Example 12, Steps A-I, but starting with 2 from Example 13, Step B instead of trans-3-(1-p-nitrobenzylcarbonyldioxyethyl)-4-(2-hydroxyethyl)-2-azetidinone, 9 is obtained.

Step L

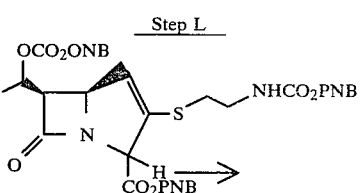

9

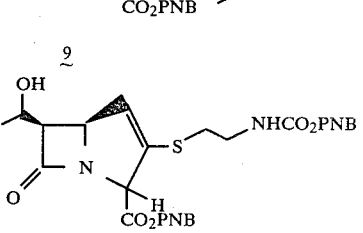

10

A solution of 40 mg of 9 (mw=765; 0.052 mmole) in 15 ml of chloroform in a water-cooled quartz vessel is flushed with N₂. The reaction vessel is then placed in a Rayonet photochemical reactor under N₂. The solution is photolyzed at 3,500 Å for 3 hrs. Concentration of the solution under a stream of N₂ is followed by chromatography on a thin-layer silica gel plate (eluant=75% EA/CHCl₃; repeated extraction of desired u.v. bands with 1% MeOH/CHCl₃). The starting material band yields 22 mg. The product band yields 8 mg of 10. Starting material is re-submitted to the reaction conditions to yield more of 10.

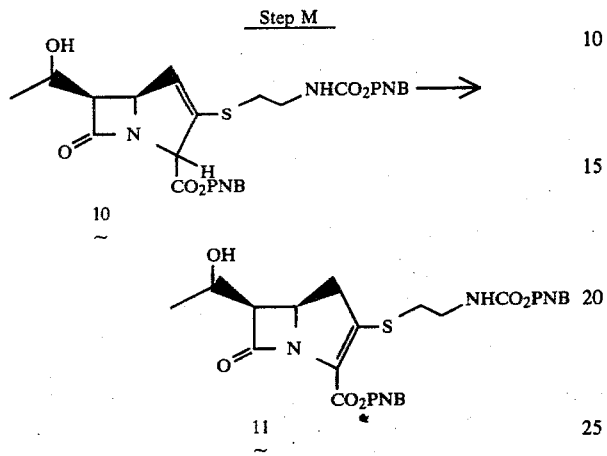

To 24 mg of 10 (mw=586; 0.041 mmole) in 0.73 ml DMSO (distilled from CaH₂ at 8 mm Hg and stored over 4A Linde molecular sieves) is added 98 μl diisopropylamine (distilled from NaH under N₂). After stirring for a few minutes, the stoppered reaction mixture is kept at r.t. for 4 hours. The amine and DMSO are then taken off under high vacuum with no external heating. After chasing a few times with EA, the resultant foam is chromatographed on a thin layer silica gel plate (eluant=75% EA/CHCl₃; repeated extraction of desired bands with CHCl₃ and EA). The product band yields 9 mg of 11. The starting material band yields 12 mg. Starting material is resubmitted to the reaction conditions to yield more of 11.

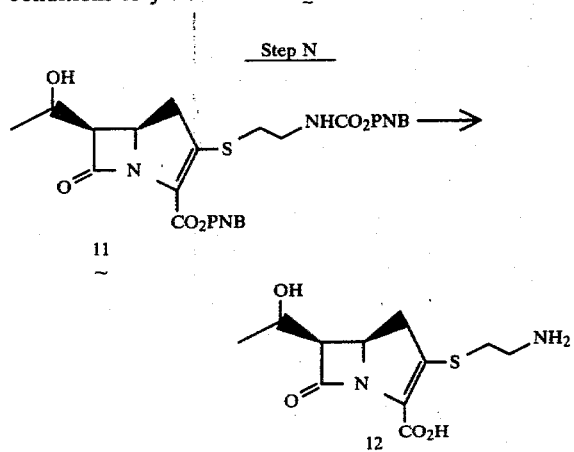

The conversion of 11 to 12 is carried out exactly as described in Example 12, Step K. The eluate from the XAD-2 column is not lyophilized directly however. Instead it is concentrated on a rotary evaporator under high vacuum and with a water bath no warmer than 30° C. to a final volume of 1–2 ml. The concentrate is then shell-frozen in a lyophilizing vial, and lyophylized overnight in a shelf lyophylizer wherein the shelf may be held at −20° C. The product exhibits an nmr spectrum in D₂O with peaks at 4.75–4.64δ(multiplet, H₈), 4.60δ(dd, J₄,₅=6.5 Hz, J₅,₆=6.5 Hz) 4.03δ(dd, J₅,₆=6.5 Hz, J₆,₈=6.5 Hz), 3.66–3.37δ(multiplet, H₄ and cysteamine methylene protons.).

The following Example specifically illustrates a preferred stereo-selective process embodiment of the present invention: As described above in detail, the starting material is a pure optical isomer of 4-vinyl-2-azetidinone (23, above). These isomers are identified as 23 (5R) and 23 (5S). In the following Example, all intermediate species in the chain of synthesis are named according to the previously introduced stereo-chemical nomenclature (see the above chart and text). In addition to the stereo-chemical symbol, such species are also named in a conventional manner in the Example.

EXAMPLE 14

Step A

Preparation of 24(5S) [1-(t-butyldimethylsilyl)-4-vinyl-2-azetidinone]

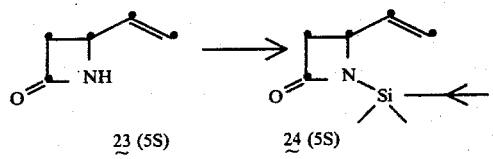

A solution of 23(5S) [4-vinyl-2-azetidinone] (1.153 g, 11.89 mmoles) and triethylamine (1.82 ml, 13.08 mmoles) in anhydrous N,N-dimethylformamide is placed under a nitrogen atmosphere, cooled to 0° C. and treated with t-butyldimethylchlorosilane (1.885 g., 12.48 mmoles) resulting in the immediate appearance of a heavy white precipitate. This mixture is stirred for one hour while gradually warming to room temperature. The mixture is partitioned between 30 ml. methylene chloride and 90 ml cold 1 M potassium dihydrogen phosphate. The aqueous phase is extracted with 20 ml methylene chloride.

The combined organic phases are washed four times with 30 ml portions of water and finally with 50 ml brine. The methylene chloride solution is dried over anhydrous magnesium sulfate and filtered. The filtrate is evaporated under reduced pressure to give 2.25 g of 24(5S) [1-(t-butyldimethylsilyl)-4-vinyl-2-azetidinone] as a colorless liquid.

NMR (CDCl₃) δ:
6.23–5.10, m, CH=CH₂
4.07, 7-line m, J=8,6 and 3 Hz, C-4H
3.35, dd, J=15 and 6 Hz, C-3H cis to C-4H
2.73, dd, J=15 and 3 Hz, C-3H trans to C-4 H
0.98, s, (CH₃)₃ C Si
0.23, s
(CH₃)₂ Si
0.18, s Following the above procedure, but making the indicated substitution, the 24(5R) isomer is obtained.

STEP B

Preparation of 25(5R,6S,8R &S) and 25(5R,6R,8R&S) [1-(t-butyldimethylsilyl)-3-(1-hydroxyethyl)-4-vinyl-2-azetidinone]

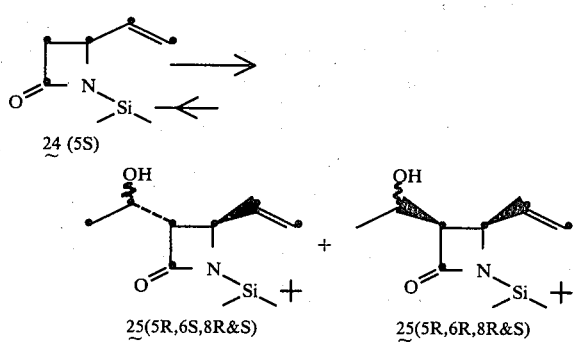

To a solution of freshly prepared lithium diisopropylamide (7.82 mmoles) in 36 ml anhydrous tetrahydrofuran under a nitrogen atmosphere at −75° C. is added a solution of 24(5S)[1-(t-butyldimethylsilyl)-4-vinyl-2-azetidinone] (1.50 g, 7.11 mmoles) in 10 ml anhydrous THF. The resulting yellow solution of the lithium enolate is, after 16 minutes, treated with acetaldehyde (1.59 ml, 28.4 mmoles). In 10 minutes, the reaction is quenched by adding 30 ml of a saturated aqueous ammonium chloride solution. This mixture is extracted with 50 ml and 25 ml portions of ethyl acetate. The combined ethyl acetate solutions are washed with 50 ml of brine and dried over anhydrous magnesium sulfate. The drying agent is removed by filtration and the filtrate is evaporated in vacuo to give the crude product as a yellow oil Purification by chromatography on silica gel eluting with 10% ethyl acetate/chloroform gives 25(5R6S8R&S) and 25(5R6R8R&S) [1-(t-butyldimethylsilyl)-3-(1hydroxyethyl)-4-vinyl-2-azetidinone]

Following the above procedure, except making the indicated substitution, the 25(5S,6R,8R&S) and 25(5S,6S,8R&S) isomers are obtained.

STEP C

Preparation of 26(5R,6S,8R) and 26(5R,6S,8S) [1-(t-butyldimethylsilyl)-3-(1-p-nitrobenzylcarbonyldioxyethyl)-4-vinyl-2-azetidinone]

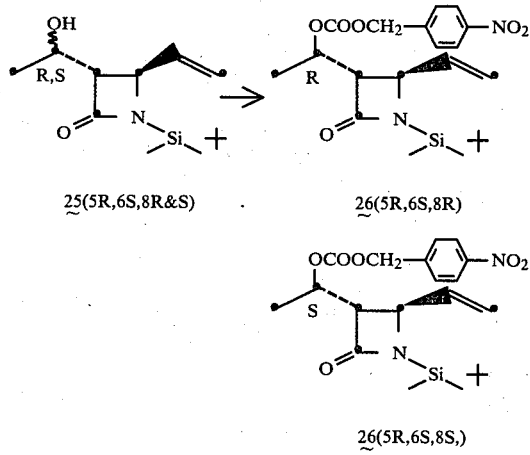

Under nitrogen at −78° C. a solution of 25(5R,6S,8R) and 25(5R,6S,8S) (56 mg, 0.220 mmole) in 1 ml of anhydrous tetrahydrofuran is treated with 2.4 M n-butyllithium in hexane (101 μl, 0.242 mmole). To this solution is added, in five minutes, a solution of p-nitrobenzyl chloroformate (52 mg, 0.242 mmole) in anhydrous tetrahydrofuran. After stirring at −78° C. for a period of 55 minutes, 10 ml of a saturated aqueous ammonium chloride solution is added and the product extracted into ethyl acetate. The combined ethyl acetate solutions are washed with brine and dried over anhydrous magnesium sulfate. The drying agent is removed by filtration, and the filtrate is evaporated in vacuo to give 91 mg of a yellow oil. Purification by preparative thick-layer chromatography on silica gel developing with 5% ethyl acetate/chloroform gives, respectively, 26(5R,6S,8R) and 26(5R,6S,8S) in 54% overall yield.

In a similar manner, the diastereomers 26(5R,6R,8S) and 26(5R,6R,8R) are obtained when the indicated substitution is made, i.e., an equivalent amount of 25(5R,6R,8R&S) replaces the 25(5R,6S,8R&S) of Step C.

Following the above procedure, but making the indicated substitution, the following diastereomers are obtained:

26(5S,6R,8R);
26(5S,6R,8S);
26(5S,6S,8R); and
26(5S,6S,8S)

STEP D

Desilylation of 26 (5R,6S,8R) to provide 27 (5R,6S,8R) [3-(1-p-nitrobenzylcarbonyldioxyethyl)-4-vinyl-2-azetidinone]

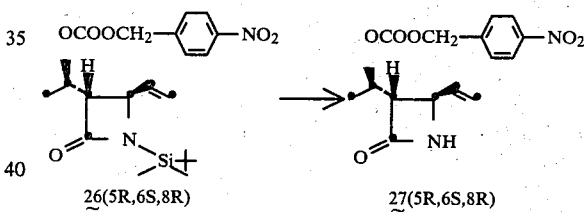

A solution of 26(5R,6S,8R) [1-(t-butyldimethylsilyl)-3-(1-p-nitrobenzylcarbonyldioxyethyl)-4-vinyl-2-azetidinone](61 mg, 0.141 mmole) in 2 ml of 0.5 N HCl/MeOH is stirred at room temperature (25° C.) for a period of 3 hours. The solution is then cooled to 0° C. and neutralized by the addition of 5 ml of 5% aqueous sodium bicarbonate. The product is extracted into ethyl acetate (10 ml, 2×5 ml). The combined ethyl acetate solutions are washed with water (2×5 ml) and 10 ml brine and then dried over anhydrous magnesium sulfate. The drying agent is removed by filtration, and the filtrate is evaporated in vacuo to give an oil. Preparative thick-layer chromatography of this material on silica gel developing with 10% ethyl acetate/chloroform gives 44 mg of 27(5R,6S,8R) [3-(1-p-nitrobenzylcarbonyldioxyethyl)-4-vinyl-2-azetidinone].

Following the procedure of Step D, except making the indicated substitution, the following isomers are obtained by desilylation:

26(5R,6R,8R)→27(5R,6R,8R)
26(5R,6R,8S)→27(5R,6R,8S)
26(5R,6S,8S)→27(5R,6S,8S)
26(5S,6R,8R)→27(5S,6R,8R)
26(5S,6R,8S)→27(5S,6R,8S)
26(5S,6S,8R)→27(5S,6S,8R)

26(5S,6S,8S)→27(5S,6S,8S)

STEP E

Preparation of 14(5S,6S,8R) via 28(5S,6S,8R) by sulfenyl halide addition and dehydrohalogenation

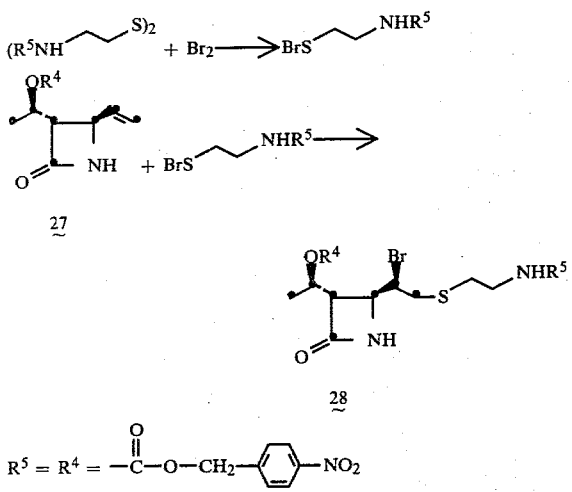

$R^5 = R^4 = -\overset{\overset{O}{\|}}{C}-O-CH_2-\underset{}{\bigcirc}-NO_2$

A solution of the N-p-nitroCBZ cysteamine disulfide, 96 mg (0.19 mmoles) in 1.5 ml THF (freshly distilled from LiAlH4) is cooled to −25° C. and treated dropwise with stirring with 0.5 ml of a solution of 135 mg Br2 in sieve dried CCl4 (2.2 ml final volume; portion added is equivalent to 0.19 mmoles of Br2). The resultant orange solution is stirred at −20° C. for 5 min. then treated with 54.0 mg of the vinyl azetidinone, 27(5R6S8R) in 0.5 ml sieve dried CH2Cl2. The color lightens to yellow. The mixture is allowed to come to 0° C. over 5-10 minutes. Examination of tlc (silica 5% MeOH in CH2Cl2 or 20% EtOAc in CH2Cl2) shows a main spot with $R_f$ and $Ce^{IV}+/H+$/heat characteristics different from either disulfide or starting 4-vinyl-2-azetidinone. The reaction mixture is concentrated to 0.5 ml under N2, streaked directly on two 8"×8" 1000μ silica GF plates, and developed with 20% EtOAc in CH2Cl2. The main band under U.V., is scraped off, and extracted with EtOAc to give 28(5S,6S,8R).

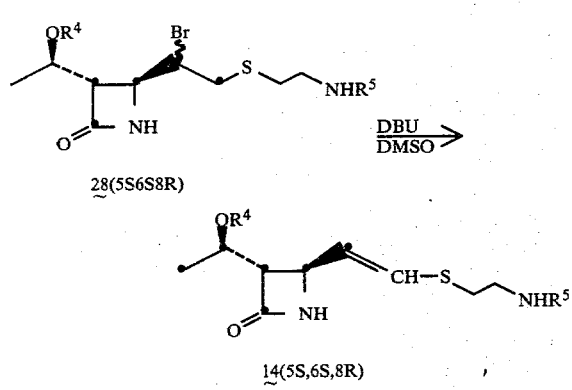

The bromosulfide, 28(5S,6S,8R), 77.0 mg (0.162 mmole) is dissolved in 1.0 ml. sieve stored DMSO (distilled from CaH2), and stirred under nitrogen while 25λ DBU (0.19 mmole) is added. After 3 hours, the mixture is poured into water/KH2PO4 and extracted repeatedly with EtOAc. The combined extracts are washed twice with water, dried with anhydrous MgSO4 and evaporated under nitrogen. The crude product, 42 mg, is streaked on an 8×8" 1000μ silica GF plate and developed with 20% EtOAc in CH2Cl2 to give 14(5S,6S,8R).

Following the above procedure except making the indicated substitution, the following isomers are obtained:

14(5R,6R,8R)
14(5R,6R,8S)
14(5R,6S,8S)
14(5S,6R,8R)
14(5S,6R,8S)
14(5R,6S,8R)
14(5S,6S,8S)

STEP F

Preparation of I(5R,6R,8R); I(5R,6S,8S); I(5R,6R,8S); I(5S,6S,8R); I(5R,6S,8R); I(5S,6R,8S); I(5S,6S,8S); and I(5S,6R,8R).

Following the exact procedure described in Example 12, Steps D-K, except making the indicated substitutions, all isomeric species 14 of Example 14 Step E, are converted to the corresponding isomeric form of I:

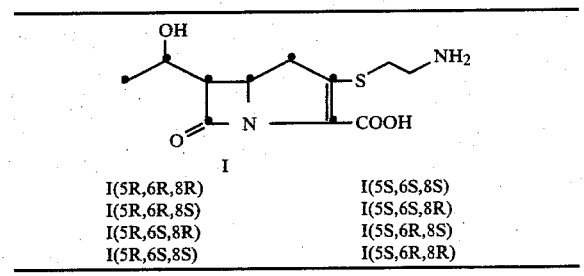

| I(5R,6R,8R) | I(5S,6S,8S) |
| I(5R,6R,8S) | I(5S,6S,8R) |
| I(5R,6S,8R) | I(5S,6R,8S) |
| I(5R,6S,8S) | I(5S,6R,8R) |

EXAMPLE 15

Preparation of Bis (p-Nitrobenzyloxycarbonylaminoethyl)disulfide

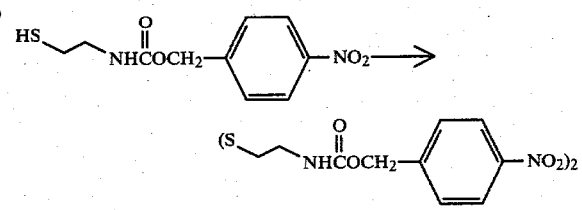

Under nitrogen at −20° C., bromine (1.21 ml, 0.022 mmole) is added to a solution of p-nitrobenzyloxycarbonylaminoethanethiol (11.28 g, 0.044 mole) in 100 ml of anhydrous tetrahydrofuran. The cooling bath is removed, and the cold solution is stirred for 15 minutes. The solution is then diluted with 400 ml ethyl acetate and washed with 200 ml 1 M pH 7 phosphate buffer, 200 ml 1 M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis (p-nitrobenzyloxycarbonylaminoethyl)disulfide:

IR (CH2Cl2) μ:
3.04 NH
5.96 carbonyl
6.22, 6.61 nitro
NMR (CDCl3) δ:

8.24 ⎫
7.54 ⎭ d, J = 8.5Hz, ArH 5.37, broad s, N<u>H</u>
5.26, s, ArC<u>H</u>₂O
3.60, q, J=6 Hz and 6 Hz, NHC<u>H</u>₂CH₂
2.86, t, J=6 Hz, NHCH₂C<u>H</u>₂S

EXAMPLE 16

STEP A

Preparation of Cis and Trans-3-(1-p-nitrobenzylcarbonyldioxyethyl)-4-[2,2-bis(2-hydroxyethyl)thioethyl]-2-azetidinone

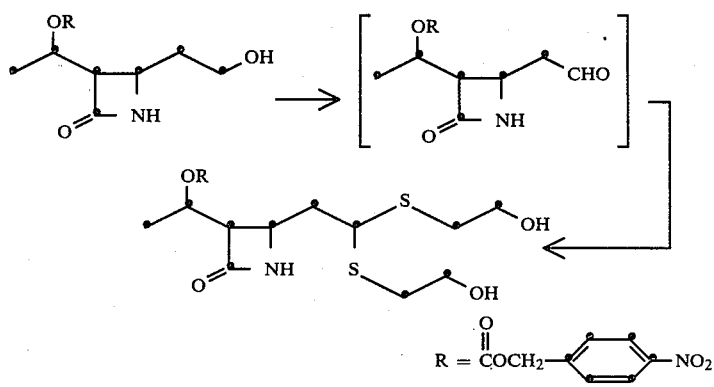

Under nitrogen at 25° C., a mixture of anhydrous pyridine (0.146 ml, 1.81 mmoles) and anhydrous, powdered chromium trioxide (92 mg, 0.916 mmole) in 8 ml anhydrous acetonitrile is stirred for a period of 30 minutes. To the resulting dark brown solution is added 250 mg of dry Supercel followed by a solution of trans-3-(1-p-nitrobenzylcarbonyldioxyethyl)-4-(2-hydroxyethyl)-2-azetidinone (186 mg, 0.550 mmole) in 1 ml anhydrous acetonitrile. After stirring for a period of 1 hour, the reaction mixture is filtered through a mixed, packed bed of 2 g each of silica gel and magnesium sulfate. The bed is washed repeatedly with a total of 30 ml of additional acetonitrile. The filtrate is concentrated under reduced pressure at 25° C. to a volume of 3 ml. By thin-layer chromatography (silica gel; ethyl acetate/benzene 2:1) this solution contains a product ($R_f$=0.38) less polar than the starting material ($R_F$=0.21).

The acetonitrile solution of trans-3-(1-p-nitrobenzylcarbonyldioxyethyl)-4-(2-oxoethyl)-2-azetidinone prepared above is, under nitrogen and at 0°, treated with 2-mercaptoethanol (0.386 ml, 5.5 mmoles) followed immediately by boron trifluoride etherate (0.176 ml, 1.43 mmoles). After stirring for a period of 15 minutes, this solution is partitioned between aqueous dipotassium hydrogen phosphate (1.5 g. in 4 ml of water) and 12 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give 229 mg of an oil. The product is purified by preparative thicklayer chromatography on silica gel developing with ethyl acetate to give 118 mg of trans-3-(1-p-nitrobenzylcarbonyldioxyethyl)-4-[2,2-bis(2-hydroxyethyl)thioethyl]-2-azetidinone as a colorless oil.

ir (CH₂Cl₂) μ:
5.75 (5.79 shoulder) β-lactam and carbonate 6.20, 6.55 nitro nmr (acetone-d₆) τ:
1.70, d, J=8.5 Hz, 2H, Ar<u>H</u>
2.28, d, J=8.5 Hz, 2H, Ar<u>H</u>
2.48–2.88, m, 1H, N<u>H</u>

4.63, s, ArCH₂ ⎫
4.63–5.12, m, CH₃C<u>H</u> ⎭ 3H 5.80, t, J = 7Hz, CH₂C<u>H</u><(S / S) ⎫
5.80–7.45, m, C-4H + C-3H + SC<u>H</u>₂CH₂OH ⎭ 13H 7.63–8.33, m, 2H, C<u>H</u>₂CH
8.53, d, J=6.5 Hz 3H, C<u>H</u>₃CH

The cis diastereoisomers are obtained in an analogous manner. Alternatively, the mixed diastereoisomers are obtained when the starting materials comprise a mixture of the diastereoisomers.

STEP B:

Preparation of Trans-3-(1-p-nitrobenzylcarbonyldioxyethyl)-4-[2,2-bis(2-azidoethyl)thioethyl]-2-azetidinone

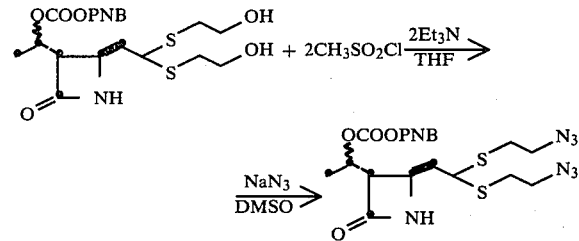

To a solution of 211 mg (mw=474; 0.445 mmole) trans-3-(1-p-nitrobenzylcarbonyldioxyethyl)-4-[2,2-bis(2-hydroxyethyl)thioethyl]-2-azetidinone in 5 ml tetrahydrofuran (THF) (distilled from lithium aluminum hydride) at 0° C. is added 103 mg mesylchloride (mw=114; 0.904 mmole) in 1 ml THF followed immediately by 134 μl triethylamine (mw=101; ρ=0.729; 0.967 mmole). The reaction mixture is stirred for 1 hour under N₂. The triethylamine hydrochloride is filtered under N₂ washing with a few milliliters additional THF. The clear colorless filtrate is concentrated under a stream of N₂ followed by pumping under high vacuum for 10 minutes. The dimesylate is immediately dissolved in 5 ml DMSO (distilled from CaH₂ at 8 mm and stored over 4A Linde Molecular sieves) in the presence of 347 mg NaN₃ (mw=65; 5.34 mmole). After stirring overnight under N₂, 10 ml H₂O and 20 ml ethyl acetate (EA) are added. The layers are separated, and the aqueous one is washed three times with 10 ml EA, each organic layer then being backwashed with 10 ml H₂O and 10 ml brine. The combined EA layers are dried over anhydrous MgSO₄, filtered and concentrated under a N₂ stream to give the crude diazide. Preparative thin layer chromatography on silica gel yields trans-3-(1-p-nitrobenzylcarbonyldioxyethyl)-4-[2,2-bis(2-azidoethylthio)ethyl]-2-azetidinone. The cis diastereoisomers or the cis-trans mixture are obtained in an analogous manner.

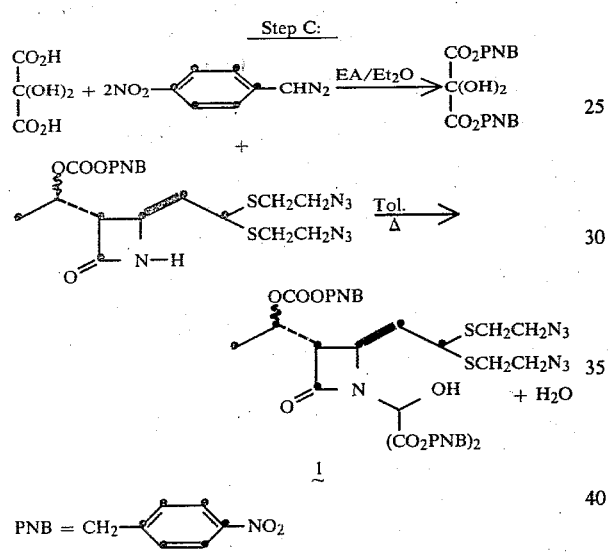

Step C:

PNB = CH₂—⟨⟩—NO₂

A freshly prepared (H. Davies and M. Schwarz, J.O.C., 30, 1242 (1965)) solution of p-nitrophenyldiazomethane (29 mmole) in 150 ml of ether is added with stirring to a solution of 1.0 g oxomalonic acid, monohydrate (mw=136; 7.35 mmole) in 50 ml ethylacetate (EA) at 0° C. After 2½ hours the yellow solution is concentrated on a rotary evaporator with mild heating to approximately half the volume, dried over anhydrous sodium sulfate, filtered and concentrated as above to an oil. To the crude p-nitrobenzyl ester in 50 ml toluene (Tol.) is added 3.54 g of trans-3-(1-p-nitronbenzylcarbonyldioxyethyl)-4-[2,2-bis(2-azidoethyl)thioethyl]-2-azetidinone (mw=524; 6.75 mmole). With stirring the reaction mixture is heated in an oil bath allowing approximately ⅓ of the toluene to boil off. Toluene (dried over 3A 1/16" Linde Molecular sieves) is added to again bring the volume to 50 ml, and the azeodrying process is repeated three additional times. The solution is then refluxed under N₂ for one hour, the azeodrying process repeated a final time, and refluxing continued for an additional hour. Concentration of the resulting solution under a stream of N₂ yields crude 1. The crude material is chromatographed on silica gel to give 1. The cis diastereoisomers of the cis-trans mixture is obtained in an analogous manner.

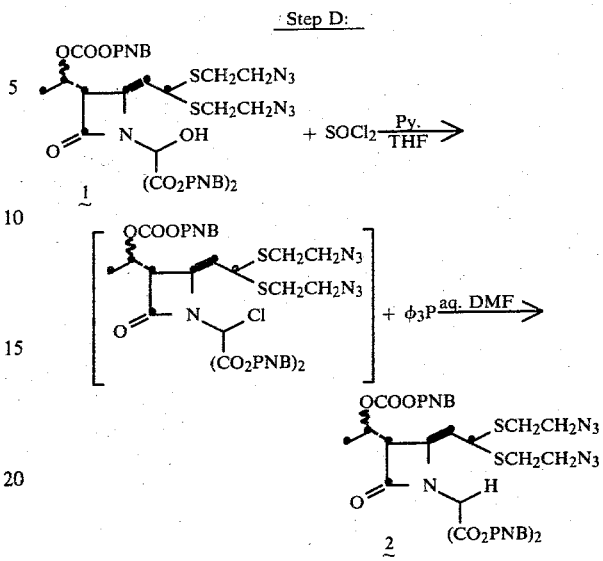

Step D:

To a solution of 2.80 g 1 (mw=912; 3.07 mmole) in 35 ml THF (distilled from lithium aluminum hydride) at −20° C. is added 0.3 ml pyridine (mw=79; ρ=0.982; 3.73 mmole) (distilled from NaH and stored over 4A Linde Molecular sieves). With stirring under N₂, 0.438 g thionyl chloride (mw=119; 3.68 mmole) in 1 ml THF is added dropwise. The reaction mixture is stirred under N₂ for 5 minutes at −20° C., then ½ hour at 0° C., and finally 1 hour at 25° C. The pyridine hydrochloride is filtered under N₂ and washed twice with benzene (dried over 3A 1/16" Linde Molecular sieves). The combined filtrate and washings are concentrated under a N₂ stream, slurried in a small volume of benzene with anhydrous MgSO₄, filtered under N₂ and then concentrated under a N₂ stream. Pumping on high vacuum for ½ hour yields an oil. To this freshly prepared chloro compound is added with stirring 0.885 g triphenyl phosphine (mw=262; 3.38 mmole) in 66 ml 9:1 dimethylformamide (DMF)/H₂O followed by 550 mg K₂HPO₄ (mw=174; 3.16 mmole). The reaction mixture is stirred at 25° C. for 35 minutes. After dilution with EA and brine, the layers are separated and the aqueous one extracted three times with EA. The combined EA layers are washed with brine, dried over anhydrous MgSO₄, filtered, and concentrated under a stream of N₂ to give crude 2. The material is chromatographed on silica gel to give 2. The cis diastereoisomers or the cis-trans mixture is obtained in an analogous manner.

Step E:

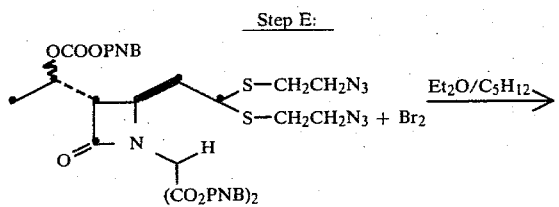

Step E:

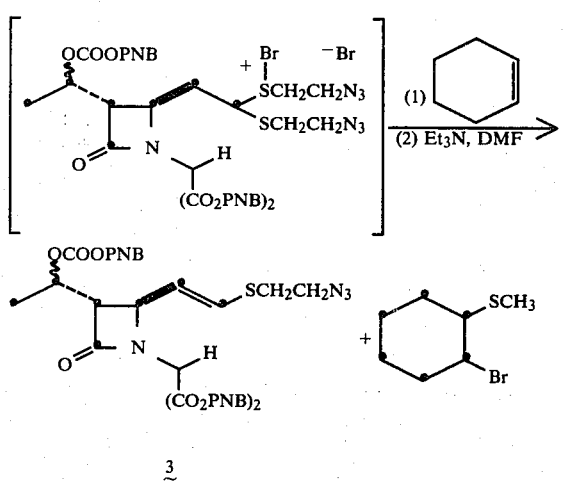

To 7.8 ml pentane (dried over 4A Linde molecular sieves) is added 0.2 ml Br$_2$ (mw=160; $\rho$=3.12; 3.9 mmole). To a solution of 950 mg $\underline{2}$ (mw=896; 1.06 mmole) in 15 ml Et$_2$O (dried over 3A 1/16" Linde molecular sieves) at 0° C. under N$_2$ with stirring is added dropwise 2.3 ml of the above 0.49 M Br$_2$ solution (1.13 mmole). After stirring for 10 minutes at 0° C., 114 μl cyclohexene (mw=82, $\rho$=0.81; 1.13 mmole) is added. After 5 minutes at 0° C., 300 μl of triethylamine (mw=101; $\rho$=0.729; 2.17 mmole) is added to the stirred reaction mixture. This is followed immediately by the addition of 14 ml ice cold DMF (distilled from anhydrous CaSO$_4$ at 40 mm and stored over 4A Linde molecular sieves). Stirring at 0° C. under N$_2$ is continued for 3 hours. The reaction mixture is poured into a stirred ice-cold mixture of 2.5 ml 1 M KH$_2$PO$_4$—40 ml H$_2$O—75 ml EA. After separation of the layers, the aqueous one is saturated with NaCl and re-extracted with EA. The combined organic layers are extracted once with brine, dried over anhydrous MgSO$_4$, filtered and concentrated under a N$_2$ stream followed by pumping on a high vacuum pump to provide crude $\underline{3}$. Preparative thin layer chromatography on silica gel yields $\underline{3}$. The cis diastereoisomers or the cis-trans mixture is obtained in an analogous manner.

Step F:

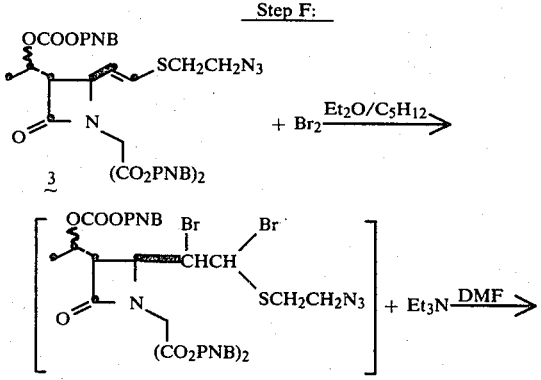

Step F:

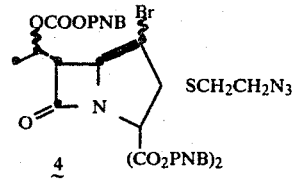

To 9.16 ml pentane (dried over 4A Linde Molecular sieves) is added 0.2 ml Br$_2$ (mw=160, 3.9 mmole). To 474 mg 3 (mw=793; 0.598 mmole) in 13 ml Et$_2$O (dried over 3A 1/16" Linde Molecular sieves) at 0° C. under N$_2$ with stirring is added dropwise 1.52 ml of the above 0.42 M Br$_2$ solution (0.63 mmole). After 15 minutes at 0° C., 337 μl Et$_3$N (mw=101; $\rho$=0.729; 2.43 mmole) is added followed immediately by the addition of 6.35 ml ice-cold DMF (distilled from anhydrous CaSO$_4$ at 40 mm and stored over 4A Linde Molecular sieves). The reaction mixture is stirred for 1½ hours at 20° C., then poured into a stirred ice-cold mixture of 1.6 ml 1 M KH$_2$PO$_4$—20 ml H$_2$O, and 20 ml EA. The layers are separated and the aqueous one saturated with NaCl and re-extracted with additional EA. The combined organic layers are washed once with brine, dried over anhydrous MgSO$_4$ and filtered. The filtrate is concentrated under a N$_2$ stream and then pumped on high vacuum to give crude $\underline{4}$. Preparative thin layer chromatography on silica gel gives $\underline{4}$. The cis diastereoisomers or the cis-trans mixture is obtained in an analogous manner.

Step G

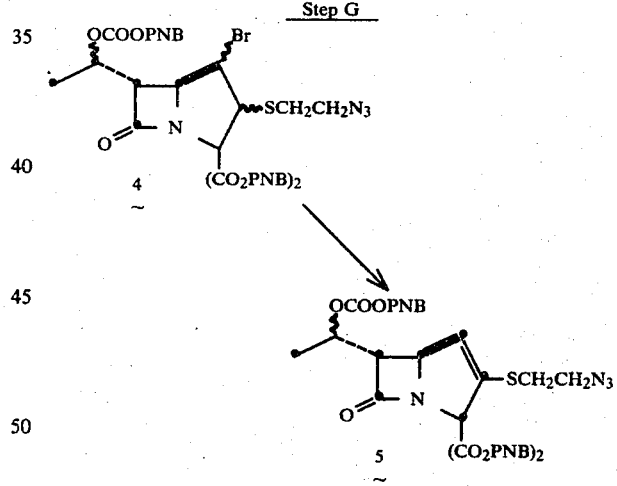

To 29 mg anhydrous silver fluoride (mw=127; 0.23 mmole) is added a solution of 122 mg of $\underline{4}$ (mw=871; 0.14 mmole) in 3.5 ml anhydrous pyridine. The stoppered reaction mixture is stirred at room temperature in the dark for one hour and then poured into 20 ml cold water—30 ml EA. After separation of the layers, the aqueous one is extracted two times with EA and one time with CHCl$_3$. Each organic layer is extracted one time with H$_2$O and one time with brine. The combined organic layers are dried over anhydrous MgSO$_4$, filtered, and concentrated under a N$_2$ stream followed by pumping on high vacuum to give crude $\underline{5}$. Preparative thin layer chromatography on silica gel yields $\underline{5}$. The cis diastereoisomers or the cis-trans mixture is obtained in an analogous manner.

Step H:

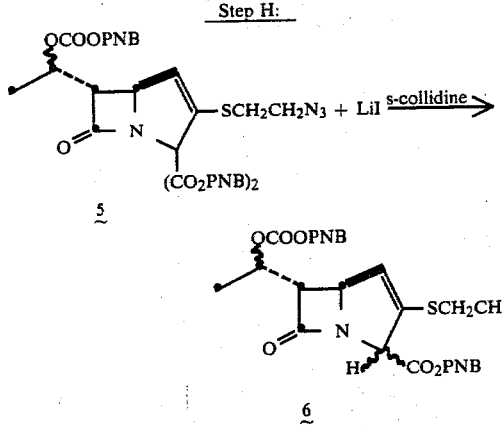

A solution of 187 mg 5 (mw=791; 0.236 mmole) in 2.5 ml s-collidine (distilled from powdered KOH at 30 mm pressure) is added to 45 mg anhydrous LiI (dried for a few hours at 100° C. over P₂O₅ under vacuum) (mw=134; 0.336 mmole). With stirring under N₂, the reaction mixture is heated in an oil bath at 120° C. After a total of 25 minutes, the reaction mixture is cooled to 25° C., diluted with CH₂Cl₂ and transferred to a round bottom flask for concentration under a N₂ stream and then on high vacuum. Partitioning of the residue between 10 ml EA and 1.8 ml 1 M KH₂PO₄ in 10 ml H₂O is followed by extraction of the aqueous layer two additional times with EA. The combined organic layers are extracted with brine, dried over anhydrous MgSO₄, filtered and concentrated under a stream of N₂ to give crude 6. Preparative thin layer chromatography on silica gel yields 6. The cis diastereoisomers or the cis-trans mixture is obtained in an analogous manner.

Step I:

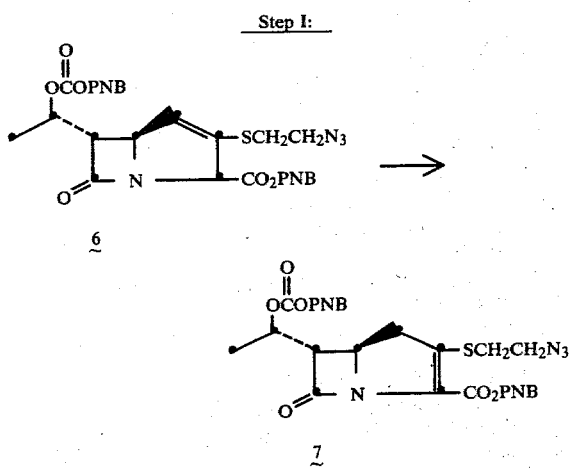

To 39 mg of 6 (mw=612; 0.064 mmole) in 0.7 ml DMSO (distilled from CaH₂ at 8 mm and stored over 4A Linde molecular sieves) is added 100 μl diisopropyl-amine (distilled from NaH under N₂ and stored over 4A Linde molecular sieves) (Mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a column of silica gel (packed, applied, and eluted with EA) to remove resid-ual DMSO. After concentration under a N₂ stream of all fractions having u.v. absorbance, the material is chromatographed on a thin layer silica gel plate. The product band yields 7.

Step J:

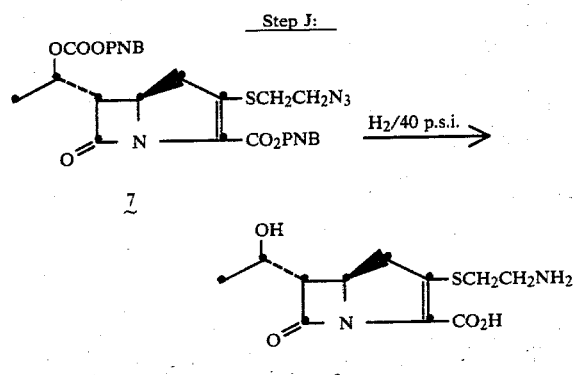

In the presence of 61 mg PtO₂, 61 mg of 7 (mw=612; 0.1 mmole) in 6 ml dioxane, 6 ml THF, 3 ml H₂O is hydrogenated at 40 p.s.i.—H₂ for 4 hours. The reaction mixture is then filtered through Celite washing with 2 ml 0.1 N pH 7 phosphate buffer. After concentration in vacuo to the cloud point, the aqueous mixture is extracted with ethyl acetate. The water layer is concentrated to a small volume and applied to a column of 100 g XAD-2 resin. Upon elution with H₂O and discarding the initial fractions, those fractions containing product are lyophilized to give 8. The cis diastereomers on the cis-trans mixture is obtained in an analogous manner.

EXAMPLE 17

Preparation of Pharmaceutical Compositions

One such unit dosage form consists in mixing an equimolar mixture of (5R6S8S)- and (5S6R8R)-3-(2-aminoethylthio)-6-(1-hydroxyethyl)-7-oxo-1-azabicyclo[3.2.0-]hept-2-ene-2-carboxylic acid [I(16)] with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
| --- | --- |
| I(16) | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

|  | PER TABLET |
|---|---|
| PARENTERAL SOLUTION | |
| Ampoule: | |
| I(16) | 500 mg. |
| Diluent: Sterile Water for Injection | 2 cc. |
| OPTHALMIC SOLUTION | |
| I(16) | 100 mg. |
| Hydroxypropylmethyl Cellulose | 5 mg. |
| Sterile Water     to | 1 ml. |
| OTIC SOLUTION | |
| I(16) | 100 mg. |
| Benzalkonium Chloride | 0.1 mg. |
| Sterile Water     to | 1 ml. |
| TOPICAL OINTMENT | |
| I(16) | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

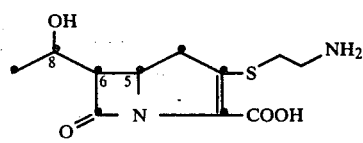

which has the absolute configuration 5S,6S,8R and the pharmaceutically acceptable salts thereof.

2. A compound having the structural formula:

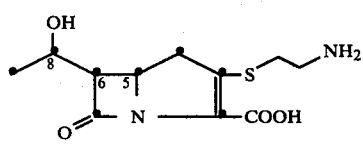

which has the absolute configuration 5R,6R,8R and the pharmaceutically acceptable salts thereof.

3. A compound having the structural formula:

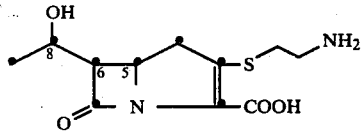

which has the absolute configuration 5S,6S,8S and the pharmaceutically acceptable salts thereof.

4. A compound having the structural formula:

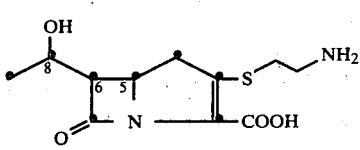

which has the absolute configuration 5S,6R,8R and the pharmaceutically acceptable salts thereof.

5. A compound having the structural formula:

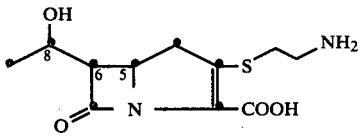

which has the absolute configuration 5S,6R,8S and the pharmaceutically acceptable salts thereof.

6. A mixture comprising two or more isomers of a compound having the structural formula:

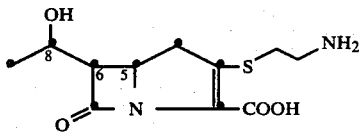

which isomers, in terms of their absolute configuration relative to the above structure are selected from the group consisting of: 5R,6R,8S; 5S,6S,8R; 5R,6R,8R; 5S,6S,8S; 5R,6S,8S; 5S,6R,8R; 5R,6S,8R; and 5S,6R,8S.

7. An antibiotic pharmaceutical composition comprising a therapeutically effective amount of a compound according to claim 1 and a pharmaceutical carrier therefor.

8. An antibiotic pharmaceutical composition comprising a therapeutically effective amount of a compound according to claim 2 and a pharmaceutical carrier therefor.

9. An antibiotic pharmaceutical composition comprising a therapeutically effective amount of a compound according to claim 3 and a pharmaceutical carrier therefor.

10. An antibiotic pharmaceutical composition comprising a therapeutically effective amount of a compound according to claim 4 and a pharmaceutical carrier therefor.

11. An antibiotic pharmaceutical composition comprising a therapeutically effective amount of a compound according to claim 5 and a pharmaceutical carrier therefor.

12. An antibiotic pharmaceutical composition comprising a therapeutically effective amount of the mixture according to claim 6 and a pharmaceutical carrier therefor.

* * * * *